(12) United States Patent
Nakatsugawa et al.

(10) Patent No.: US 7,910,115 B2
(45) Date of Patent: Mar. 22, 2011

(54) POLYPEPTIDE ABSORBABLE INTO DIGESTIVE ORGANS

(75) Inventors: Shigekazu Nakatsugawa, Aichi (JP); Hideaki Nakamura, Aichi (JP)

(73) Assignee: Shigekazu Nakatsugawa, Aichi (JP)

( * ) Notice: Subject to any disclaimer, the term of this patent is extended or adjusted under 35 U.S.C. 154(b) by 806 days.

(21) Appl. No.: 10/554,789

(22) PCT Filed: Apr. 30, 2004

(86) PCT No.: PCT/JP2004/006344
§ 371 (c)(1),
(2), (4) Date: Jul. 17, 2006

(87) PCT Pub. No.: WO2004/096843
PCT Pub. Date: Nov. 11, 2004

(65) Prior Publication Data
US 2007/0183975 A1    Aug. 9, 2007

(30) Foreign Application Priority Data
Apr. 30, 2003 (JP) .................................. 2003-125917

(51) Int. Cl.
*A61K 39/07* (2006.01)
(52) U.S. Cl. .................. 424/246.1; 424/193.1; 435/4
(58) Field of Classification Search ........................ None
See application file for complete search history.

(56) References Cited

U.S. PATENT DOCUMENTS

| 5,437,988 A | 8/1995 | Bellini et al. |
| 5,939,315 A | 8/1999 | Adams et al. |

FOREIGN PATENT DOCUMENTS

| EP | 0 409 098 | 1/1991 |
| JP | 62-500215 | 1/1987 |
| WO | 86/01825 | 3/1986 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
M.L. Stahl et al., "Replacement of the *Bacillus subtilis* subtilisin structural gene with an in vitro-derived deletion mutation", Journal of Bacteriology, vol. 158, No. 2, pp. 411-418, May 1984.
T. Nakamura et al., "Nucleotide sequence of the subtilisin NAT gene, aprN, of *Bacillus subtilis* (natto)", Biosci. Biotech. Biochem., vol. 56, No. 11, pp. 1869-1871, 1992.

* cited by examiner

*Primary Examiner* — Jennifer E Graser
(74) *Attorney, Agent, or Firm* — Wenderoth, Lind & Ponack, L.L.P.

(57) ABSTRACT

A polypeptide absorbable into digestive organs, which is linked with a bioactive polypeptide, and assists absorption of the bioactive polypeptide into digestive organs when it is orally taken; a fusion polypeptide comprising the polypeptide absorbable into digestive organs and the bioactive polypeptide; and an oral composition comprising the fusion polypeptide are provided.

2 Claims, 14 Drawing Sheets

POLYPEPTIDE ABSORBABLE INTO DIGESTIVE ORGANS

This application is a U.S. national stage of International Application No. PCT/JP2004/006344 filed Apr. 30, 2004.

TECHNICAL FIELD

The invention of this application relates to a novel polypeptide absorbable into digestive organs that can achieve a drug's efficacy by realizing high absorption of a bioactive polypeptide via oral administration. In addition, the invention of this application relates to a composition such as an oral drug product or a functional food product containing a fusion polypeptide of the polypeptide absorbable into digestive organs and a bioactive polypeptide.

BACKGROUND ART

In the postgenomic era, the structures or functions of human proteins, which are sometimes said to be 100,000 or more types, are being elucidated, and many proteins that can become a component of a remedy for disease (drug proteins) have been identified. On the other hand, however, the fact is that the route of administration of a therapeutic protein is generally by way of injection only. Injection is considered rather appropriate during hospitalization or on a hospital visit in the acute phase of disease, however it is not easy to maintain blood concentration by injection administration in any case except for drip injection. Therefore, administration at a medical institute becomes a premise except for limited protein formulations and medical care cost becomes expensive compared with the case of oral administration. Further, in many cases using injection, stresses such as pain are unavoidable especially for such as pediatric patients. In addition, consecutive injection administration on consecutive days often involves with changes in tissues such as a hard lump around the injection site. Further, not a small amount of medical wastes such as containers for injection solution and injection syringes are produced and costs are incurred for such reasons. For these reasons, great expectation is placed on oral administration in the chronic phase of disease. Because of this, the methodology for absorption via oral mucosa or the methodology for covering, coating or the like with a chemical material to prevent digestion is coming to be used practically. However, in the present situation, an absorption rate in oral administration hardly exceeds 30% even in these methodologies in most cases. For example, Clement S. et al. reported the results of clinical trials by the oral administration of insulin (Phases I and II) and the absorption rate of insulin by oral administration is less than 30% (Clement S. et al. Metabolism. January 2004; 53(1): 54-58).

Nattokinase is an enzyme (protease) produced by *Bacillus subtilis natto* (*Bacillus subtilis*), and an invention utilizing its thrombolytic effect (e.g., JP-A-2002-360220) has been known. However, it is not known that this nattokinase highly efficiently realizes the transfer of a bioactive polypeptide from the digestive organs into the blood stream.

DISCLOSURE OF THE INVENTION

An object of the present invention is to provide a novel technical means capable of realizing absorption of a protein (a bioactive protein or peptide), which is not absorbed through the digestive tract, in the body via oral administration.

A first invention to achieve the above object is a polypeptide absorbable into digestive organs, which is linked with a bioactive polypeptide, and assists absorption of the bioactive polypeptide into digestive organs when it is orally taken.

One aspect of the first invention is a polypeptide having a sequence comprising at least 100 consecutive amino acids of *Bacillus subtilis* nattokinase, or a sequence in which several amino acid residues within said sequence have been deleted, added or replaced with another amino acid residue. Further more specifically, it is a polypeptide having a sequence comprising at least 100 consecutive amino acids of the SEQ ID NO:2, or a sequence in which several amino acid residues within said sequence have been deleted, added or replaced with another amino acid residue.

A second invention is a fusion polypeptide comprising the polypeptide absorbable into digestive organs and a bioactive polypeptide.

A third invention is a labeled fusion polypeptide comprising the polypeptide absorbable into digestive organs, and a drug-candidate substance and a labeling substance.

A fourth invention is a polynucleotide encoding the polypeptide absorbable into digestive organs of the first invention. Specific examples include a polynucleotide comprising a sequence having at least 300 consecutive nucleotides of SEQ ID NO:1.

A fifth invention is an expression vector, which has the polynucleotide of the fourth invention and expresses the polypeptide absorbable into digestive organs.

A sixth invention is a fusion polynucleotide comprising the polynucleotide of the fourth invention and a polynucleotide encoding a bioactive polypeptide.

A seventh invention is an expression vector having the fusion polynucleotide of the sixth invention.

An eighth invention is an oral composition containing the fusion polypeptide of the second invention.

A ninth invention is a method for in vivo toxicity testing of a test substance, which comprising orally administering a complex of the polypeptide the first invention and a test substance to an animal.

A tenth invention is a kit for in vivo toxicity testing of a test substance, which comprising a complex of the polypeptide of the first invention and a test substance.

That is, the present inventor has confirmed that several functional food products containing a glycoprotein as a main component have a therapeutic effect on a disease state via oral administration so far. Therefore, a plan for using such a protein as a carrier for a therapeutic protein that has a physiological activity but is not absorbable through the digestive tract thereby enabling its oral administration which was difficult so far was designed, and this plan was actually realized, thus the present invention was completed.

Incidentally, "bioactive polypeptide" in this invention is referred to as a polypeptide, which is not absorbed through the digestive organ by itself or is difficult to exhibit the original physiological activity (e.g., conservation, promotion or suppression of the physiological function of a living organism, improvement of a disease state, or the like) through the digestive organ. In addition, "absorbable into the digestive organs" means that a substance that travels in the blood stream through the digestive tract exhibits its original physiological activity.

In addition, "protein" or "polypeptide" means a molecule composed of a plurality of amino acid residues, which are bound to one another by natural amide bonds (peptide bonds) or by residue bonds other than natural amide bonds. Further, "polynucleotide" means a molecule in which phosphate esters of nucleosides in which a purine or a pyrimidine is attached to a sugar via a β-N-glycosidic bond (ATP, GTP, CTP and UTP; or dATP, dGTP, dCTP and dTTP) are bound to one another. Specific examples include genomic DNA encoding a protein, mRNA transcribed from genomic DNA, cDNA synthesized from mRNA and the like. In addition, it may be a double strand or a single strand. Further, they include a sense strand and an antisense strand of such a genomic DNA, mRNA or cDNA.

Other terms and concepts in the respective inventions of this application will be defined in detail in the description of the embodiments or Examples of the invention. In addition, various techniques to be used for implementing this invention can be easily and surely carried out by those skilled in the art based on a known literature or the like except for the techniques whose sources are particularly specified. For example, preparation of a drug of this invention is described in Remington's Pharmaceutical Sciences, 18th Edition, ed. A. Gennaro, Mack Publishing Co., Easton, Pa., 1990, and techniques of genetic engineering and molecular biology are described in Sambrook and Maniatis, in Molecular Cloning: A Laboratory Manual, Cold Spring Harbor Laboratory Press, New York, 1989; Ausubel, F. M. et al., Current Protocols in Molecular Biology, John Wiley & Sons, New York, N.Y., 1995 and the like. Further, the terms in this invention are basically according to IUPAC-IUB Commission on Biochemical Nomenclature or based on the meanings of terms used conventionally in this field.

BEST MODE FOR CARRYING OUT THE INVENTION

Figure 1:
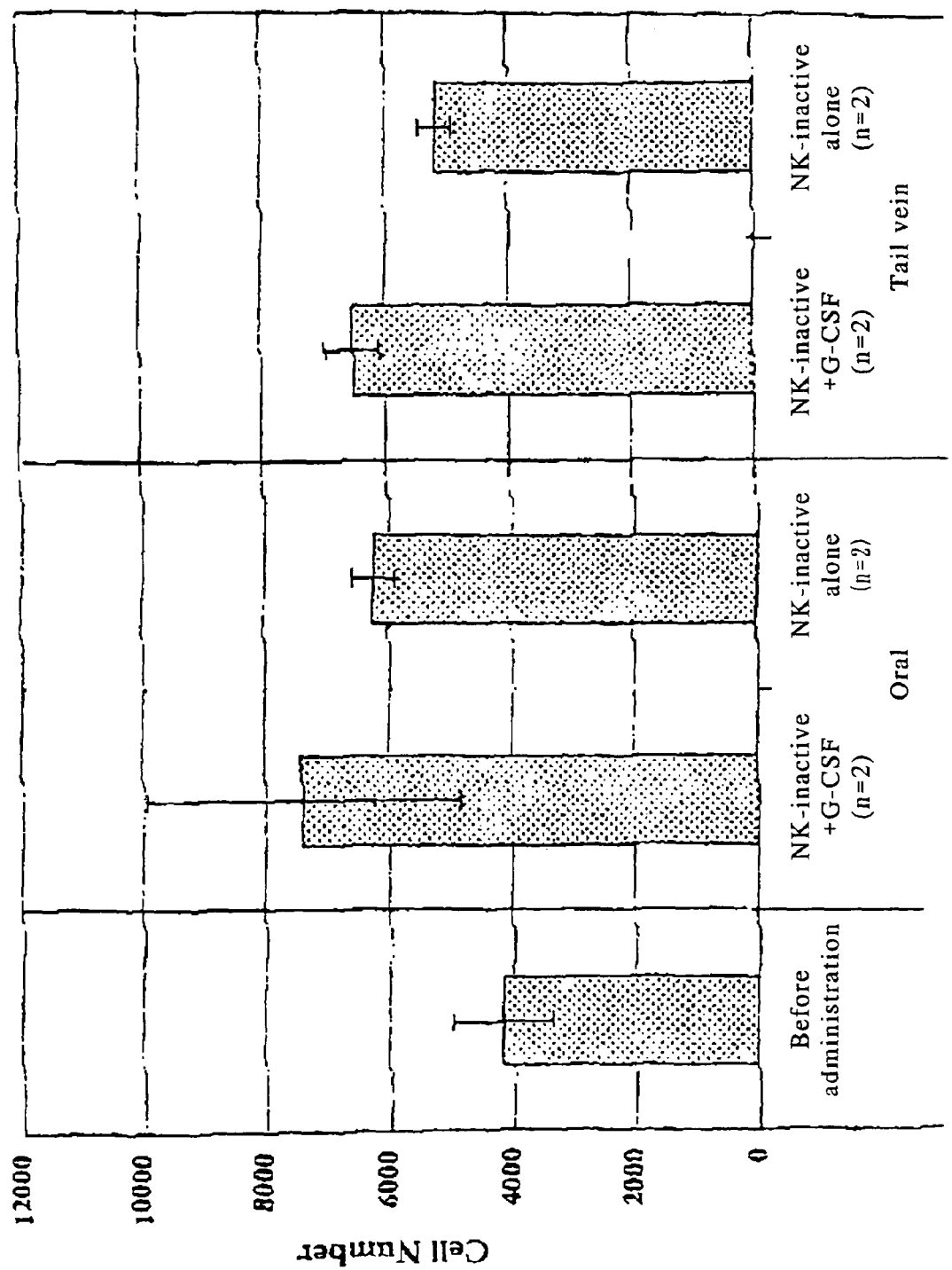
FIG. 1 is a graph showing the effects of oral administration of NK+ G-CSF fusion polypeptide on the number of peripheral blood nucleated cells of mice being not irradiated with X-rays.

As described above, the polypeptide absorbable into digestive organs of this invention is characterized in that when it is orally taken with a linked bioactive polypeptide that is not absorbable through the digestive tract by itself, it realizes absorption of the bioactive polypeptide through the digestive tract. As such a polypeptide, for example, a polypeptide comprising the same amino acid sequence as that of a glycoprotein (e.g., CAF: caipo antidiabetic fraction, LEM: Lentinus edodes mycelia or the like) contained in a functional food product, which is known to exhibit an effect on improving a disease state by oral administration can be exemplified, and particularly a polypeptide comprising substantially the same amino acid sequence as that of a protease (nattokinase) derived from *Bacillus subtilis* is preferred.

As for the nattokinase, various types are known, and they can be used without restriction. In this invention, however, a nattokinase whose amino acid sequence is shown in SEQ ID NO:2 is provided as one example. That is, this polypeptide absorbable into digestive organs of this invention is selected as, for example, a sequence comprising the full-length of SEQ ID NO:2 (381 amine acids), a sequence comprising arbitrary 100 amino acids of SEQ ID NO:2, a sequence comprising arbitrary 101 to 150 amino acids thereof, a sequence comprising arbitrary 151 to 200 amino acids thereof, a sequence comprising arbitrary 201 to 250 amino acids thereof, a sequence comprising arbitrary 251 to 300 amino acids thereof, a sequence comprising arbitrary 301 to 350 amino acids thereof, or a sequence comprising arbitrary 351 to 380 amino acids thereof. Particularly, a sequence comprising 100 or more amino acids from the N-terminal side is preferred, or it may be the one comprising the amino acids from the 20th (Met) to the 326th (Tyr). In addition, this polypeptide may be the one having a sequence in which a plurality of amino acid residues have been deleted, added or replaced with another amino acid residue within the scope of not deteriorating its ability of assisting digestive organ absorption. The phrase "a plurality of amino acid residues" in this case means, for example, 1 to about 30 amino acid residues.

Such a polypeptide absorbable into digestive organs can also be produced based on, for example, a known amino acid sequence of *Bacillus subtilis* nattokinase (NK) (e.g., SEQ ID NO:2 or an amino acid sequence of GenBank/AF368283) by a known peptide synthesis method (Merrifield, R. B. J. Solid phase peptide synthesis I. The synthesis of tetrapeptide. J. Amer. Chem. Soc. 85, 2149-2154, 1963; Fmoc Solid Phase Peptide Synthesis. A Practical Approach, Chan, W. C. and White, P. D., Oxford University Press, 2000). In addition, the synthesis can also be performed automatically by using, for example, ABI431A peptide synthesizer (Applied Biosystem) or the like.

Such a synthetic polypeptide may be the one comprising residue bonds other than natural amide bonds or the one comprising unnatural residues instead of natural amino acid residues. As the residue bonds other than natural amide bonds, for example, chemical bonds or coupling means such as glutaraldehyde, N-hydroxysuccinimide esters, bifunctional maleimides, N,N'-dicyclohexylcarbodiimide (DCC) or N,N'-diisopropylcarbodiimide (DIC) can be exemplified. In addition, linking groups that can be an alternative to the peptide bonds include, for example, ketomethylene (e.g., —C(=O)—NH— for —C(=O)—CH$_2$—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester are included (see, e.g., Spatola (1983) in Chemistry and Biochemistry of Amino Acids, Peptides and Proteins, Vol. 7, pp 267-357, "Peptide Backbone Modifications," Marcell Dekker, N.Y.).

On the other hand, with regard to the unnatural amino acid residue, an aromatic amino acid can be produced by substitution with, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, in which an alkyl may be a substituted or unsubstituted methyl, ethyl, propyl, hexyl, butyl, pentyl, isopropyl, iso-butyl, sec-isotyl, iso-pentyl or a non-acidic amino acid. Aromatic rings of an unnatural amino acid include, for example, thiazolyl, thiophenyl, pyrazolyl, benzimidazolyl, naphthyl, furanyl, pyrrolyl, and pyridyl aromatic rings. In the case of an acidic amino acid, it can be produced by substitution with, for example, a non-carboxylate amino acid while maintaining a negative charge; (phosphono)alanine; or sulfated threonine. Carboxyl side groups (e.g., aspartyl or glutamyl) can also be selectively modified by a reaction with a carbodiimide (R'—N=C=N—R') such as, for example, 1-cyclohexyl-3(2-morpholinyl-(4-ethyl)carbodiimide or 1-ethyl-3(4-azonia-4,4-dimetholpentyl)carbodiimide.

Aspartyl or glutamyl can also be converted to asparaginyl or glutaminyl residue by a reaction with an ammonium ion. As for a basic amino acid, it can be produced by substitution with, for example, (in addition to lysine and arginine) an amino acid, ornithine, citrulline, or (guanidino)-acetic acid, or (guanidino)alkyl-acetic acid, in which the alkyl is defined above. A nitrile derivative (e.g., containing the CN-moiety in place of COOH) can be substituted for asparagine or glutamine. Asparaginyl and glutaminyl residues can be deaminated to the corresponding aspartyl or glutamyl residue. An unnatural arginine residue can be produced by reacting arginyl with, for example, one or more reagents, including, for example, phenylglyoxal, 2,3-butanedione, 1,2-cyclohexanedione, or ninhydrin, preferably under alkaline conditions. In the case of a tyrosine residue, it can be produced by reacting tyrosyl with, for example, an aromatic diazonium compound or tetranitromethane. N-acetylimidizol and tetranitromethane can be formed by using O-acetyl tyrosyl species and 3-nitro derivatives, respectively. An unnatural cysteine residue can be produced by reacting a cysteinyl residue with, for example, an α-haloacetate such as 2-chloroacetic acid or chloroacetamide and a corresponding amine; to give a carboxymethyl or a carboxyamidomethyl derivative. An unnatural cysteine residue can also be produced by reacting a cysteinyl residue with, for example, bromo-trifluoroacetic acid, α-bromo-β-(5-imidozoyl)propionic acid; chloroacetyl phosphate, N-alkylmaleimide, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. An unnatural lysine can be produced (or an amino terminal residue can be altered) by reacting lysinyl with, for example, a succinic anhydride or another carboxylic acid anhydride. Lysine and another α-amino-containing residue mimetic can also be produced by a reaction with an imidoester, such as methyl picolinimidate, pyridoxal phosphate, pyridoxal, chloroborohydride, trinitrobenzenesulfonic acid, O-methylisourea or 2,4-pentanedione, and a reaction catalyzed by a transamidase with glyoxylate. An unnatural methionine can be produced by a reaction with, for example, methionine sulfoxide. Unnatural prolines include, for example, pipecolic acid, thiazolidine carboxylic acid, 3- or 4-hydroxy proline, dehydroproline, 3- or 4-methylproline, and 3,3,-dimethylproline. An unnatural histidine residue can be produced by reacting histidyl with, for example, diethylprocarbonate or para-bromophenacyl bromide. Other unnatural amino acid residues include, for example, those produced by hydroxylation of proline and lysine; phosphorylation of a hydroxyl group of a seryl or threonyl residue; methylation of an α-amino group of lysine, arginine and histidine; acetylation of an N-terminal amine;

methylation of a main chain amide residue or substitution with an N-methyl amino acid; amidation of a C-terminal carboxyl group, and the like.

The polypeptide absorbable into digestive organs of this invention can also be obtained by a genetic engineering method utilizing a polynucleotide encoding the polypeptide (the fourth invention). For example, RNA is prepared by in vitro transcription from a recombinant expression vector having the polynucleotide, and in vitro translation is performed using this RNA as a template, whereby a target polypeptide of this invention can be obtained. In addition, the polypeptide can be expressed from a prokaryotic cell such as *E. coli* or *Bacillus subtilis*, a eukaryotic cell such as yeast, an insect cell or a mammalian cell transformed with the recombinant expression vector.

The polynucleotide for expressing the polypeptide by genetic engineerings can be used by, for example, obtaining NK cDNA utilizing a known sequence (e.g., SEQ ID NO:1) encoding *Bacillus subtilis* nattokinase (NK) (e.g., probe hybridization to a cDNA library or a PCR method), and cutting out the coding region of the polypeptide from the NK cDNA with a restriction enzyme or the like. Alternatively, the polynucleotide encoding the polypeptide can be synthesized in vitro by well-known chemical synthesis techniques as described (e.g., Carruthers (1982) Cold Spring Harbor Symp. Quant. Biol. 47: 411-418; Adams (1983) J. Am. Chem. Soc. 105: 661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68: 109; Beaucage (1981) Tetra. Lett. 22: 1859; U.S. Pat. No. 4,458,066).

In the case where the polypeptide is expressed by in vitro translation using such a polynucleotide, a recombinant expression vector (the fifth invention) is produced by inserting the polynucleotide into a vector having an RNA polymerase promoter and this vector is added to an in vitro translation system such as a rabbit reticulocyte lysate or a wheat germ extract containing an RNA polymerase corresponding to the promoter, whereby a target polypeptide can be produced in vitro. As the RNA polymerase promoter, T7, T3, SP6 and the like can be exemplified. As the vector containing such an RNA polymerase promoter, pKA1, pCDM8, pT3/T7 18, pT7/3 19, pBluescript II and the like can be exemplified.

In the case where the polypeptide is expressed in a microorganism such as *E. coli*, an expression vector (the fifth invention) is produced by recombining the polynucleotide into a vector having a replication origin in a microorganism, a promoter, a ribosome binding site, DNA cloning sites, a terminator or the like, a host cell is transformed with this expression vector, and the obtained transformant is cultured, whereby a large amount of polypeptide encoded by the polynucleotide can be expressed in a microorganism. At this time, the target polypeptide can be obtained by expressing it as a fusion protein with another protein, and separating the target polypeptide. As the expression vector for *E. coli*, a pUC system, pBluescript II, a pET expression system, a pGEX expression system and the like can be exemplified.

In the case where the polypeptide is expressed in a eukaryotic cell, a recombinant vector (the fifth invention) is produced by inserting the polynucleotide into an expression vector for a eukaryotic cell having a promoter, a splicing site, a poly(A) addition site or the like, and the recombinant vector is introduced into a eukaryotic cell, whereby a target polypeptide can be expressed in a transformed eukaryotic cell. As the expression vector, pKA1, pCDM8, pSVK3, pMSG, pSVL, pBK-CMV, pBK-RSV, EBV vector, pRS, pcDNA3, pMSG, pYES2 and the like can be exemplified. In addition, when pIND/V5-His, pFLAG-CMV-2, pEGFP-N1, pEGFP-C1, pCMV-Myc, pCMV-HA or the like is used as an expression vector, the polypeptide can also be expressed as a fusion protein to which any of a variety of tags such as a His tag, a FLAG tag, a GFP tag, a myc tag and an HA tag has been added. As the eukaryotic cell, a cultured mammalian cell such as a monkey kidney cell COS7 and Chinese hamster ovary cell CHO, budding yeast, dividing yeast, a silkworm cell, a *xenopus* oocyte and the like are usually used, however, any eukaryotic cell may be used as long as it is able to express a desired polypeptide. In order to introduce such an expression vector into a host cell, a known method such as an electroporation method, a calcium phosphate method, a liposome method, and a DEAE dextran method can be employed.

In order to isolate and purify the target polypeptide from the culture after expressing the polypeptide in a prokaryotic cell or a eukaryotic cell, it can be performed by combining known separation procedures. Examples thereof include, for example, treatment with a denaturation reagent such as urea or with a surface active agent, ultrasonic treatment, enzymatic digestion, salting-out and solvent precipitation method, dialysis, centrifugation, ultrafiltration, gel filtration, SDS-PAGE, isoelectric focusing electrophoresis, ion exchange chromatography, hydrophobic chromatography, affinity chromatography, reversed phase chromatography and the like.

The second invention is a fusion polypeptide containing the above-mentioned polypeptide and a bioactive polypeptide. That is, this fusion polypeptide is the one containing one molecule of polypeptide absorbable into digestive organs and one molecule of bioactive polypeptide as one embodiment. In addition, as another embodiment, it is the one containing 2 or more molecules of polypeptides absorbable into digestive organs and one molecule of the bioactive polypeptide. Further, as another embodiment, it is the one containing one molecule of polypeptide absorbable into digestive organs and 2 or more molecules of the same bioactive polypeptide. As still further another embodiment, it may be the one containing 1 or 2 or more molecules of polypeptides absorbable into digestive organs and 1 or 2 or more molecules of different 2 or more types of bioactive polypeptides for the respective polypeptide molecules. However, in the case of considering the absorption rate through the digestive tract, it is preferred that the molecular weight thereof is an arbitrary molecular weight of not more than 80,000 Da.

Such a fusion polypeptide can be produced by, for example, directly binding the polypeptide absorbable into digestive organs with a bioactive polypeptide via, for example, a divalent crosslinking agent (e.g., EDC, β-alanine or the like). Alternatively, the fusion polypeptide can also be produced by preparing a fusion polynucleotide (the sixth invention) in which a polynucleotide encoding the polypeptide absorbable into digestive organs is linked with a polynucleotide encoding a bioactive polypeptide, recombining it into an appropriate expression vector (the seventh invention), and expressing the fusion polynucleotide by the same genetic engineering method as described above.

As the bioactive polypeptide, a protein which is not absorbable through the digestive tract when it is taken orally by itself, and does not exhibit a physiological activity as desired in vivo can be adopted without exception. For example, it is a polypeptide comprising substantially the same amino acid sequence as that of a protein (drug protein) that directly acts on maintenance of homeostasis, prevention or improvement of any disease state. In addition, it may be a polypeptide comprising substantially the same amino acid sequence as that of, for example, a "DNA-binding protein". As the DNA-binding protein, for example, a protein (transcription factor) regulating expression of a gene associated with maintenance of homeostasis, prevention of disease (e.g., suppression of cancer) or the like, a protein promoting cleavage, modification, change in structure or change in topology of a gene DNA associated with modulation of homeostasis or disease and the like by binding to part of an intracellular gene DNA are exemplified. Of course, the bioactive polypeptide in this invention is not limited to these, and a polypeptide having any physiological activity can be adopted without restriction. However, in the case where such a bioactive polypeptide is produced by chemical synthesis or genetic engineering and a fusion polypeptide with the polypeptide absorbable into digestive organs is produced, the one whose amino acid sequence and/or the sequence of the polynucleotide encoding it is known is preferred.

Still further, the bioactive polypeptide may be the full length thereof or may be a partial peptide associated with the physiological activity thereof. Further, either of the polypeptide absorbable into digestive organs or the bioactive polypeptide may be located at the N-terminal side. In addition, the polypeptide absorbable into digestive organs and the bioactive polypeptide may be linked consecutively, or a peptide linker comprising 2 to 10 amino acid residues may be interposed therebetween.

For example, as the fusion polypeptide containing one molecule of the polypeptide absorbable into digestive organs and one molecule of the bioactive polypeptide, for example, a fusion polypeptide (NK+ G-CSF) of a partial peptide of NK and a granulocyte-colony stimulating factor (G-CSF), a fusion polypeptide (NK+ Ins) of a partial peptide of NK and insulin (Ins), a fusion polypeptide (NK+ EPO) of a partial peptide of NK and erythropoietin (EPO), a fusion polypeptide (NK+ Adiponectin) of a partial peptide of NK and adiponectin, a fusion peptide (NK+ IL) of a partial peptide of NK and interleukin and the like are exemplified, however, the fusion polypeptide of this invention is not limited to these. In addition, as examples of the fusion polynucleotide for producing such a fusion polypeptide by genetic engineering, a fusion polynucleotide comprising a partial cDNA of NK (part of SEQ ID NO:1) and a partial cDNA of mouse G-CSF (SEQ ID NO:3), a fusion polynucleotide comprising a partial cDNA of NK (part of SEQ ID NO:1) and mouse Ins2 cDNA (SEQ ID NO:4), a fusion polynucleotide comprising a partial cDNA of NK (part of SEQ ID NO:1) and mouse EPO cDNA (SEQ ID NO:5), a fusion polynucleotide (SEQ ID NO:6) comprising a partial cDNA of NK and mouse G-CSF cDNA, a fusion polynucleotide (SEQ ID NO:7) comprising a partial cDNA of NK and mouse Ins2 cDNA, a fusion polynucleotide (SEQ ID NO:8) comprising a partial cDNA of NK and mouse Ins2 cDNA, and a fusion polynucleotide (SEQ ID NO:9) comprising a partial cDNA of NK and mouse adiponectin cDNA can be exemplified, however, the fusion polynucleotide of this invention is not limited to these.

The fusion polypeptide of the second invention as described above can be formulated into, for example, an oral preparation by itself. In addition, in this case, the fusion polypeptide or the polypeptide absorbable into digestive organs and/or the bioactive polypeptide, which are part of the fusion polypeptide, may be made in the form of "salt". Examples of the salt include, for example, pharmaceutically acceptable acid (inorganic acid or organic acid) addition salts such as hydrochloride, hydrobromide, sulfate, nitrate, acetate, nitrate benzoate, maleate, fumarate, succinate, tartrate, citrate, oxalate, methanesulfonate, toluenesulfonate, aspartate and glutamate.

The third invention of this application is a labeled fusion polypeptide comprising the polypeptide absorbable into digestive organs of the first invention, a candidate substance of a drug component and a labeling substance. That is, this labeled fusion polypeptide is useful in verifying the in vivo dynamics (absorption through the digestive organs or the degree of decomposition) of the candidate substance of a drug component in, for example, the proteomics drug discovery or the like by oral intake at the level of experimental animal. The candidate substance of a drug component in the labeled fusion polypeptide is not particularly limited, and a component to become a target for general drug discovery such as an organic or inorganic compound, a protein, a peptide or the like can be adopted. In addition, in the case where the dynamics of the candidate substance is tested using a tissue specimen isolated from an experimental animal as a target, for example, an enzyme, a radioisotope, a fluorescent dye or the like can be used as the labeling substance. The enzyme is not particularly limited as long as it meets the conditions in which it has a high turnover number, it is stable even if it is bound to a fusion polypeptide, it colored a substrate specifically and the like, and an enzyme to be used in a common enzyme immunoassay such as peroxidase, β-galactosidase, alkaline phosphatase, glucose oxidase, acetylcholinesterase, glucose-6-phosphate dehydrogenase, or malate dehydrogenase can also be used. In addition, an enzyme inhibitor, a coenzyme or the like can also be used. Such an enzyme and a fusion polypeptide can be bound by a known method using a crosslinking agent such as a maleimide compound. As the substrate, a known substance can be used according to the type of an enzyme to be used. For example, in the case where peroxidase is used as an enzyme, 3,3',5,5'-tetramethylbenzidine can be used, and in the case where alkaline phosphatase is used as an enzyme, p-nitrophenol or the like can be used. As the radioisotope, the one used in a common RIA such as $^{125}$I, or $^{3}$H can be used. As the fluorescent dye, the one used in a common fluorescence method such as fluorescein isothiocyanate (FITC), or tetramethylrhodamine isothiocyanate (TRITC) can be used.

On the other hand, in order to test the dynamics of a drug-candidate substance in an animal body, for example, a metal such as manganese or iron can also be used as a labeling substance. A fusion polypeptide labeled with such a metal is administered in the body, and the metal is measured by MRI or the like, whereby the in vivo dynamics of the candidate substance can be accurately understood.

The eighth invention is an oral composition containing the fusion polypeptide of the second invention or a salt thereof. This composition is a composition in the form of being taken from the oral cavity and absorbed through the digestive organs, and examples thereof include food and drink products, oral drug products and the like. More specific examples include functional food products, health supplements, nutritional food products, nutritional supplements or others for preventing disease or alleviating symptoms, or drugs for treating disease, which exert a drug efficacy due to the bioactive polypeptide contained in the fusion polypeptide. Incidentally, since the fusion polypeptide of this invention comprises the polypeptide absorbable into digestive organs derived from CAF, LEM, NK or the like which is used as a functional food product and a physiologically active polypeptide which has been confirmed not to have toxicity within a common range of intake, there is no problem in the safety as a component of a food and drink product or a drug product.

As the remedy, it is preferred to formulate it into, for example, a tablet, a capsule, a granule, a subtle granule, a powder, or an oral liquid preparation such as a suspension or a syrup. As a carrier, a common pharmaceutical adjuvant, such as, for example, a binder (syrup, gum arabic, gelatin, sorbit, tragacanth, polyvinyl pyrrolidone, hydroxypropyl cellulose or the like), a diluent (lactose, a sugar, corn starch, calcium phosphate, sorbit, glycine or the like), a lubricant (magnesium stearate, talk, polyethylene glycol, silica or the like), a disintegrator (potato starch, carboxymethyl cellulose or the like) or a wetting agent (sodium lauryl sulfate or the like) can be used. A flavor such as strawberry flavor or peppermint or the like can also be added. In addition, a tablet can be coated by a standard method. An oral liquid preparation can be formulated into an aqueous solution or a dry product. Such an oral liquid preparation may contain a standard additive such as, for example, a preservative (methyl p-hydroxybenzoate, propyl p-hydroxybenzoate, sorbic acid or the like).

The content of the fusion polypeptide that is a therapeutic component can be adopted depending on the degree of symptoms or the dosage form, however, it can be set within the range of generally from 5 to 100% (w/w), preferably from 10 to 60% (w/w). In addition, the dose of the drug varies depending on the age, body weight or symptoms of a patient or the like, however, it can be set to about 100 to 200 mg/kg/day in terms of the amount of the fusion polypeptide.

In the case of a composition such as a food and drink product, it can be produced by adding the fusion polypeptide in the existing production process so as not to deteriorate its activity. Examples of such a food and drink product include, for example, drink products such as soft drink products, nutritional drink products, fruit drink products and lactic acid drink products (including concentrated stock solution and/or modified powder for preparing such drink products); frozen dessert such as ice cream and sherbet; processed products of grains such as soba (buckwheat noodles), udon (thick white noodles), bread, rice cakes and pasta wrapping for Chinese meat dumplings; sweets such as sugarplums, candies, chocolates, snacks, biscuits, cookies, crackers, jelly and jam; processed fish and livestock products such as boiled fish sausages, puffy cakes made of ground fish, ham and sausages; dairy products such as processed milk, cheese and butter; oils and fats and processed oils and fats products such as margarine, lard and mayonnaise; seasonings such as soy sauce, sauce, fermented soybean paste, ponzu sauce, powdered seaweed broth and powdered soup; a variety of dishes; pickles; other nutritional and health supplements in a variety forms and the like, however, it is needless to say that they are limited to these.

A therapeutic drug comprising a fusion polypeptide as described above or an oral composition containing a fusion polypeptide can exhibit a therapeutic effect equal to or higher than the case where a physiologically active polypeptide is administered by, for example, injection. For example, in the case where a fusion polypeptide containing insulin, it normalizes the blood glucose level of a patient with diabetes or the like and has an effect on prevention or treatment of glucose intolerance, diabetes (such as type 2 diabetes), insulin resistant syndrome (such as insulin receptor abnormality), polycystic ovary syndrome, hyperlipidemia, atherosclerosis, cardiovascular disease (such as angina pectoris or heart failure), hyperglycemia, hypertension, angina pectoris, pulmonary hypertension, congestive heart failure, diabetes complication (e.g., such as diabetic gangrene, diabetic arthropathy, diabetic glomerulosclerosis, diabetic dermopathy, diabetic neuropathy, diabetic cataract or diabetic retinopathy), or dermopathy, dysgeusia and the like.

The ninth invention is a method for in vivo toxicity testing of a test substance, comprising orally administering a complex of the polypeptide absorbable into digestive organs of the first invention and a test substance to an animal. The test substance in this case is, for examples, a substance which is difficult to be absorbed through the digestive tract, but is absorbed little by little over long periods of time by being contained in a food or drink product, thereby possibly adversely affecting the body. According to the method of this ninth invention, it is possible to absorb the toxic amount of such toxic substance that is not absorbable through the digestive organ through the digestive tract of an animal in a short period, whereby it becomes possible to examine the toxicity of the toxic substance at an individual level. In addition, when a complex of the polypeptide absorbable into digestive organs and a test substance is labeled with an arbitrary labeling substance, the cumulative amount of the test substance in the body can be measured by the signal of the labeling substance, and the correlation between the cumulative amount of the test substance in the body and the damage at an individual level can also be accurately understood.

The tenth invention is a test kit for conveniently performing the above-mentioned method of the ninth invention. For example, this test kit can be composed of the complex of the polypeptide absorbable into digestive organs and the test substance, a reagent for confirming that the test substance exhibits in vivo toxicity, and the like. For example, in the case where an in vivo metabolite of the test substance has toxicity or in the case where an in vivo protein of the test substance is abnormally degraded thereby having toxicity, such a reagent can be composed of an immunoassay reagent (e.g., ELISA) for determining such a metabolite thereof or an abnormal protein and the like.

EXAMPLES

Hereunder, the invention of this application will be described in more detail and specifically with reference to Examples, however, the invention of this application is not limited to the following examples.

Example 1 cDNA Cloning of Recombinant Nattokinase (NK)

Genomic DNA was prepared from *Bacillus subtilis natto* using DNeasy Tissue Kit (QUIAGEN), and the full-length KN cDNA was amplified by PCR using the genomic DNA as a template. Specifically, PCR primers were designed based on a known NK mRNA sequence (GenBank/AY219901: SEQ ID NO:1), and PCR was carried out using KOD plus (TOYOBO) with the genomic DNA as a template. After the molecular weight of the PCR product was confirmed by electrophoresis, the PCR product was cloned into pPCR-Script vector (INVITROGEN), and the sequence was confirmed.

Example 2

Preparation of Fusion Polypeptide

A fusion polypeptide was prepared in an in vitro transcription/translation system (cell-free system). Three types of NK cDNAs in which the stop codon was removed and the His tag sequence was attached were inserted at the EcoRV/XhoI site of pEU3-NII vector included in PROTEIOS Wheat germ cell-tree protein synthesis core kit manufactured by TOYOBO, respectively. That is, expression vectors in which any of cDNA encoding the full-length NK (381 amino acids), cDNA encoding the active NK (363 amino acids) obtained by deleting 19 amino acids from the C-terminus of the full-length NK, and cDNA encoding the inactive NK (294 amino acids) obtained by further deleting 69 amino acids from the C-terminus of the active NK was inserted were constructed.

Subsequently, a polynucleotide (cDNA) encoding any of the following bioactive polypeptides was inserted and ligated at the XhoI/SmaI cloning site of each expression vector.
(1) cDAN encoding part (deleting 30 amino acids at the N-terminus) of mouse granulocyte-colony stimulating factor (G-CSF) (SEQ ID NO:3)
(2) cDNA encoding the full-length mouse insulin II (Ins2) (SEQ ID NO:4)
(3) cDNA encoding the full-length of mouse erythropoietin (EPO) (SEQ ID NO:5)

Incidentally, by inserting cDNA encoding each of the above-mentioned physiologically active polypeptides, each expression vector transcribes mRNA of the fusion polypeptide in which the NK polypeptide and the physiologically active polypeptide are linked via a linker (Leu-Glu-Arg).

Subsequently, mRNA was transcribed by the reaction with Thermo T7 RNA polymerase (150 U) manufactured by TOYOBO at 37° C. for 4 hours, which was confirmed by electrophoresis. Then, by using the transcribed mRNA (12 µg), a fusion polypeptide was obtained by the translation reaction at 26° C. for 24 hours. The obtained fusion polypeptide was electrophoresed on SDS-PAGE and confirmed by Coomassie blue staining. In addition, the fusion polypeptide was confirmed by Western blotting using a His tag antibody.

The following 9 types of fusion polypeptides were obtained.
NK-full+G-CSF
NK-active+G-CSF
NK-inactive+G-CSF
NK-full+Ins2
NK-active+Ins2
NK-inactive+Ins2
NK-full+EPOF
NK-active+EPO
NK-inactive+EPO Example 3

Oral Administration of NK+ G-CSF Fusion Polypeptide

NK+ G-CSF fusion polypeptide was orally administered, and the in vivo change in the physiological activity of G-CSF was examined. Incidentally, endogenous G-CSF is produced in bone marrow cells, however, in healthy immature mice at 10 weeks of age or younger, the activity of the bone marrow cells is high. In order to clearly distinguish the difference between endogenous G-CSF and orally administered G-CSF, the activity of the bone marrow cells was suppressed by prior X-ray irradiation. Specific experimental procedure was as follows.

BALB/C male mice at 5 weeks of age were irradiated on the whole body with X-rays (150 kvp, 20 mA, filte: 0.5 AI+0.3 Cu, 2.0 Gy/min). On day 14 after 4.84 Gy of irradiation, 200 µl of blood was collected from the eye cavity and stained with giemsa, and the number of nucleated cells (cell number) excluding lymphocytes in the peripheral blood was counted with a hemocytometer.

Subsequently, to each mouse receiving 4.84 Gy of irradiation, the NK-inactive+G-CSF or the NK-inactive alone (control) was orally administered in an amount of 5 µg/100 µl using a gastric tube. In addition, any of the solutions was intravenously injected in an amount of 5 µg/50 µl via the tail of the mice. As for the mice that were not irradiated with X-rays, oral administration of the same amount as that on day 14 was also carried out on day 15, and 1 hour after the administration, 200 µl of blood was collected from the eye cavity and stained with giemsa, and the number of nucleated cells (cell number) excluding lymphocytes in the peripheral blood was counted with a hemocytometer. Immediately thereafter, 500 µl of blood was collected from the heart, and the concentration of G-CSF in the blood was determined using an ELISA kit.

As for the mice receiving 4.84 Gy of irradiation, administration of the same amount as that on day 14 was also carried out on day 15 and on day 16, and 1 hour after the administration, 200µ µl of blood was collected from the eye cavity and stained with giemsa, and the number of nucleated cells (cell number) excluding lymphocytes in the peripheral blood was counted with a hemocytometer. Immediately thereafter, 500 µl of blood was collected from the heart, and the concentration of G-CSF in the blood was determined using an ELISA kit.

As a result, in the non-irradiation group, G-CSF in the blood was significantly increased by the oral administration of the NK-inactive+G-CSF fusion polypeptide. In addition, in the individual in which the concentration of G-CSF was increased to 500 pg/ml or more (about 3-fold or more compared with the control), the number of nucleated cells in the peripheral blood was increased about 1.8-fold (FIG. 1).

Figure 2:
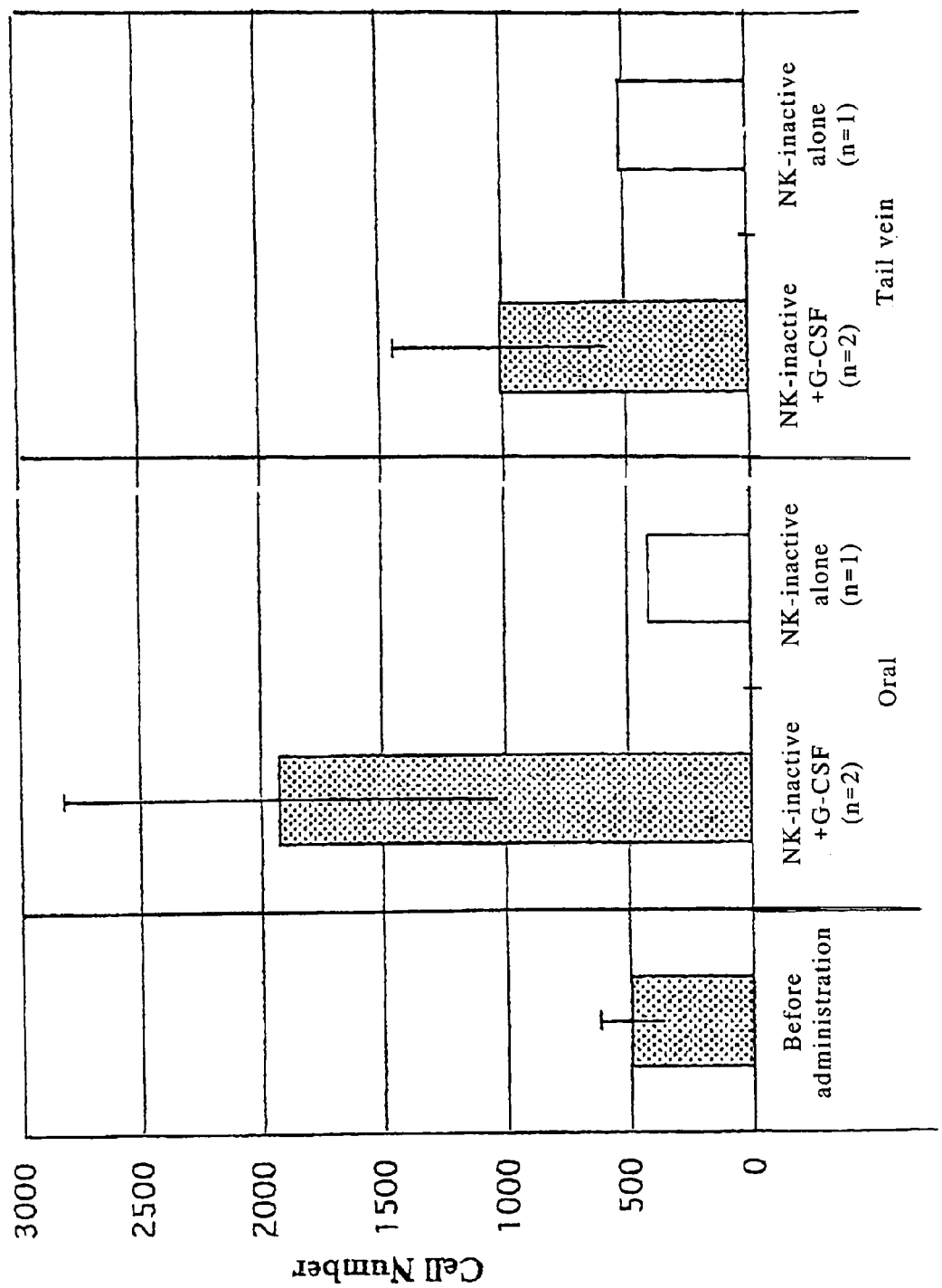
FIG. 2 is a graph showing the effects of oral administration of NK+ G-CSF fusion polypeptide on the number of peripheral blood nucleated cells of mice being irradiated with X-rays (4.84 Gy).
Figure 3:
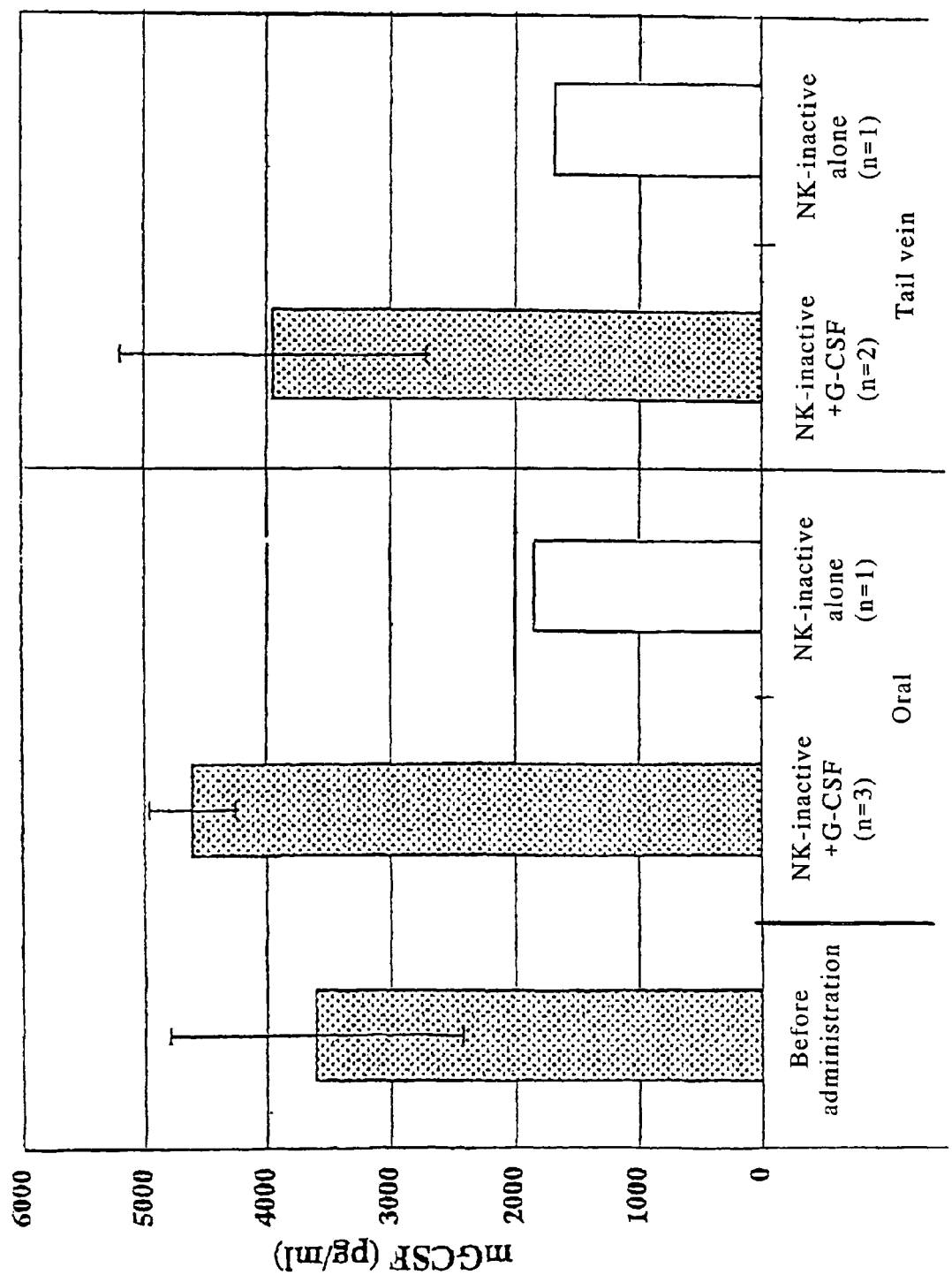
FIG. 3 is a graph showing the effects of oral administration of NK+ G-CSF fusion polypeptide on the G-CSF level in the blood of mice being irradiated with X-rays (4.84 Gy).

In addition, in the irradiation group, by the oral administration of the NK-inactive+G-CSF fusion polypeptide, G-CSF in the blood was significantly increased even as compared with the intravenous injection (FIG. 2 and FIG. 3).

Example 4

Oral Administration of NK+ EPO Fusion Polypeptide

In the same manner as in Example 3, the in vivo activity by oral administration of NK+ EPO fusion polypeptide was examined in a condition where the activity of the bone marrow cells was suppressed by X-ray irradiation.

BALB/C male mice at 5 weeks of age were irradiated on the whole body with X-rays (150 kvp, 20 mA, filte: 0.5 AI+0.3 Cu, 2.0 Gy/min). On day 12 after 3.63 Gy of irradiation, 200 µl of blood was collected from the eye cavity and the number of erythrocytes (cell number) in the peripheral blood was counted with a cell counter (SYSMEX).

Subsequently, to each mouse receiving 3.63 Gy of irradiation, the NK-inactive+EPO, the NK-active+EPO, the NK-inactive alone or the NK-active alone (control) was orally administered in an amount of 5 µg/100 µl using a gastric tube. In addition, any of the solutions was intravenously injected in an amount of 5 µg/50 µl via the tail of the mice.

Administration of the same amount as that on day 12 was carried out on day 13, and 1 hour after the administration, 200µ µl of blood was collected from the eye cavity and diluted appropriately, and the number of erythrocytes (cell number) in the peripheral blood was counted with a cell counter. Immediately thereafter, 500 µl of blood was collected from the heart, and the concentration of EPO in the blood was determined using an ELISA kit. Incidentally, as for the ELISA kit, an ELISA kit for human EPO for clinical use was used.

Figure 4:
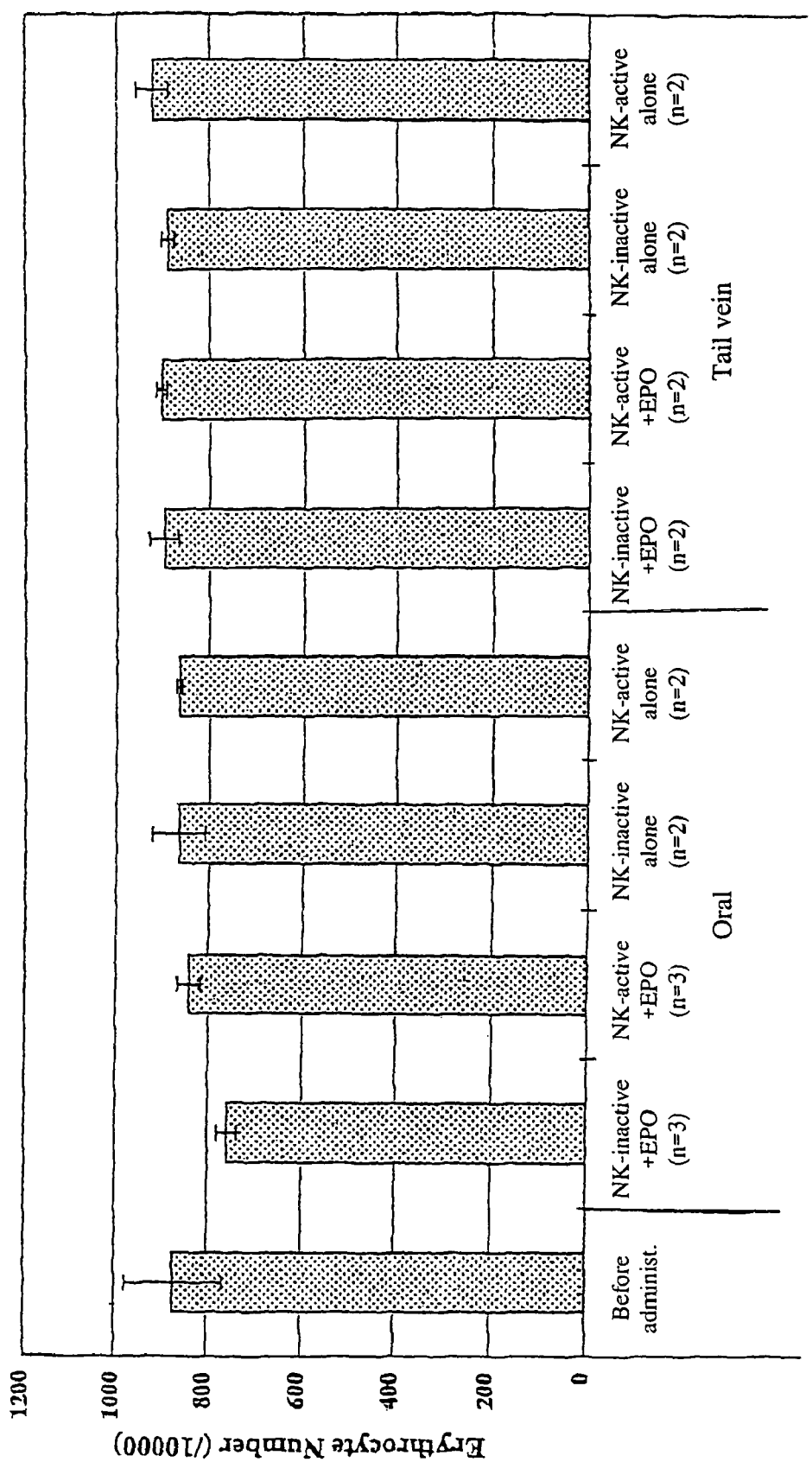
FIG. 4 is a graph showing the effects of oral administration of NK+ EPO fusion polypeptide on the number of peripheral erythrocytes of mice being not irradiated with X-rays.
Figure 5:
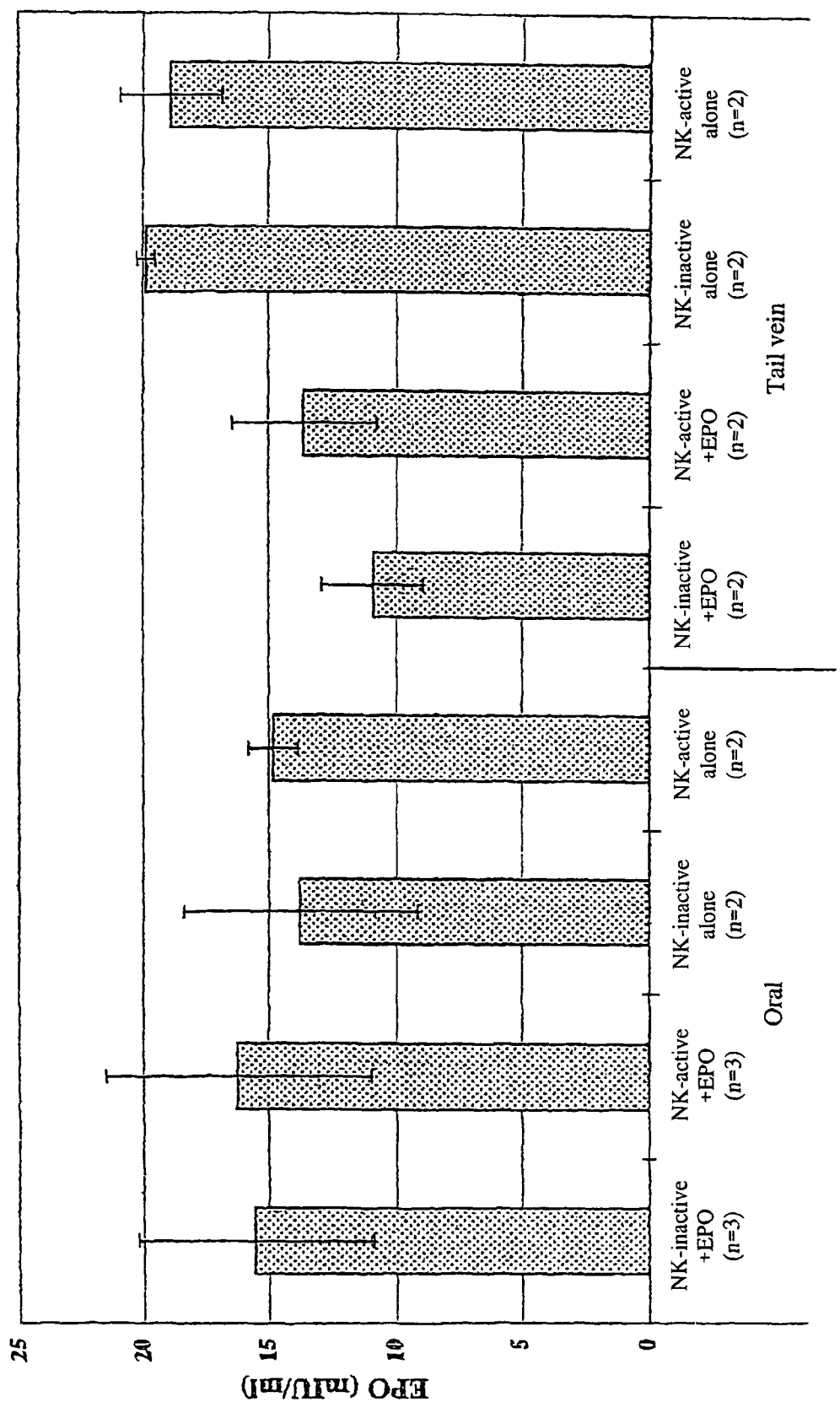
FIG. 5 is a graph showing the effects of oral administration of NK+ EPO fusion polypeptide on the EPO level in the blood of mice being not irradiated with X-rays.

The results are as follows. That is, firstly, a significant increase in the number of erythrocytes in the peripheral blood was not observed in any group (FIG. 4). In addition, from the results of ELISA, a significant increase in the concentration of EPO in the blood was not observed in any administration group (FIG. 5). Instead, there were some cases where there is a tendency of a decrease by the intravenous administration.

Figure 6:
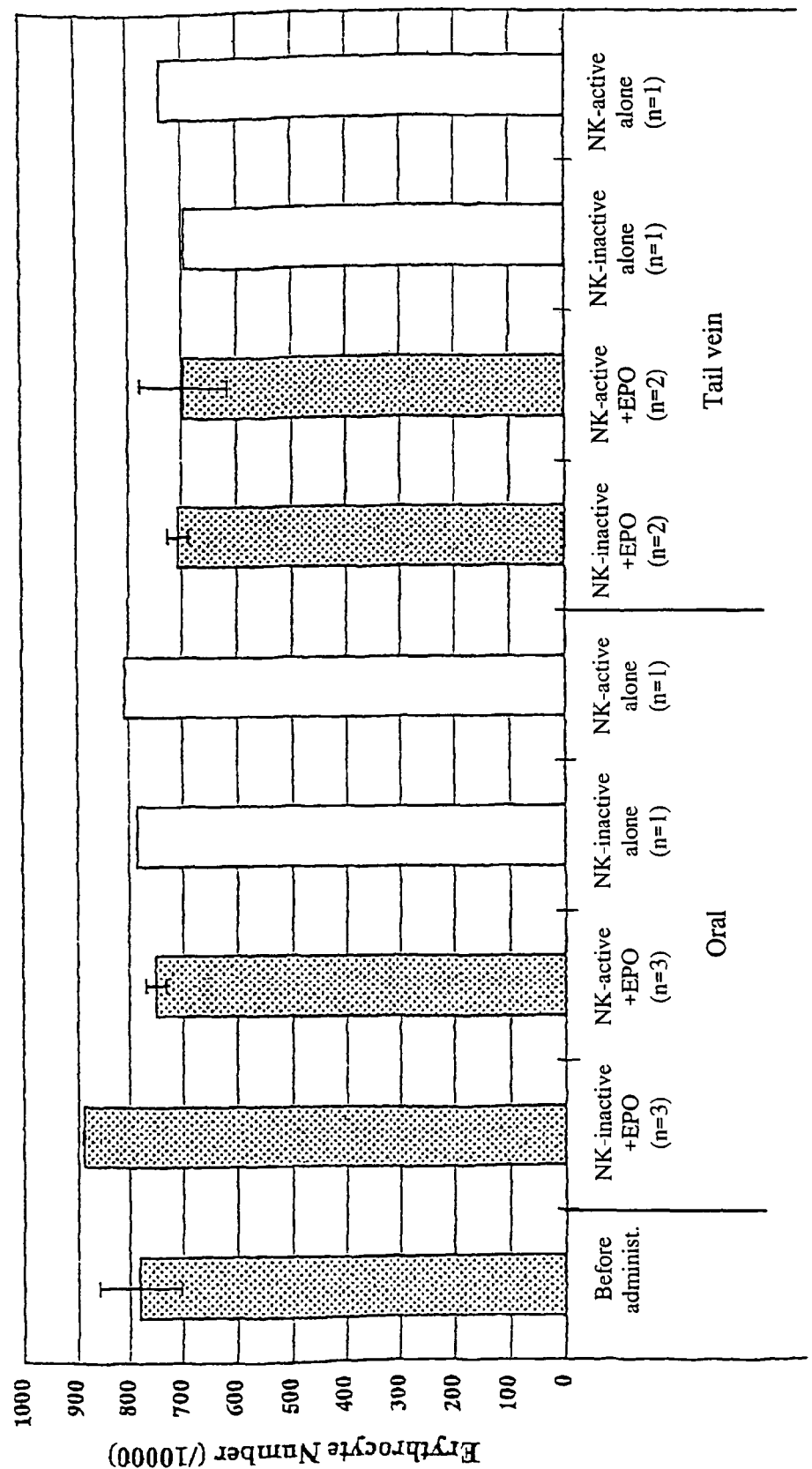
FIG. 6 is a graph showing the effects of oral administration of NK+ EPO fusion polypeptide on the number of peripheral erythrocytes of mice being irradiated with X-rays (3.634 Gy).
Figure 7:
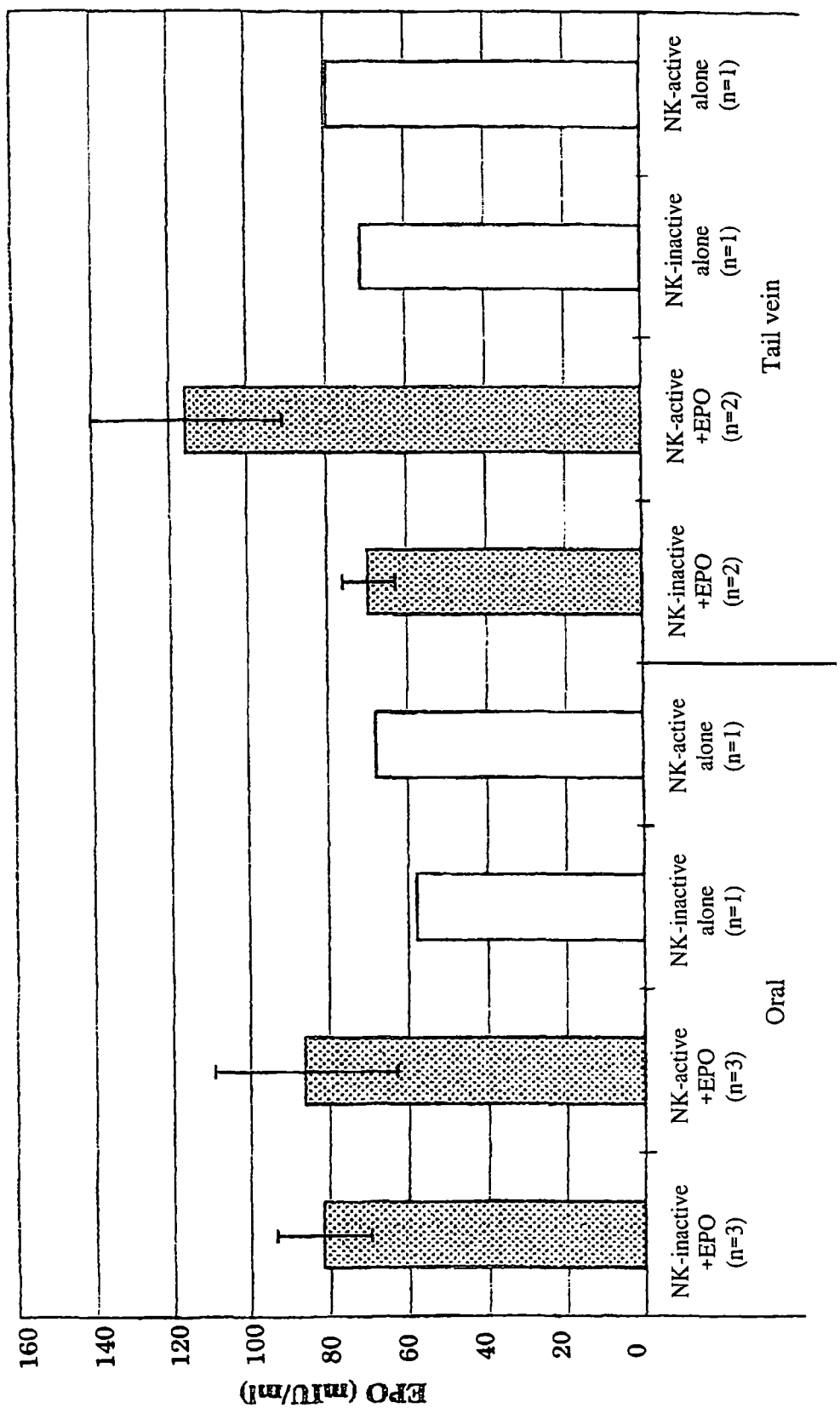
FIG. 7 is a graph showing the effects of oral administration of NK+ EPO fusion polypeptide on the EPO level in the blood of mice being irradiated with X-rays (3.634 Gy).

In the X-ray irradiation group, as for the cell number, an effect on a significant increase in the number of erythrocytes was observed by the oral administration of the NK-inactive+ EPO as compared with the intravenous injection (FIG. 6). Further, it was confirmed that in the case of the oral administration of the NK-inactive+EPO, the concentration of EPO is higher than the case of the control group (the NK-inactive alone and the NK-active alone), and the transfer rate into the blood in the oral administration of the NK-active+EPO is relatively higher than that in the intravenous administration (FIG. 7). On the other hand, in the NK-active+EPO, transfer into the blood was not necessarily favorable compared with the intravenous administration.

From the above results, it was confirmed that in the case of EPO, a higher drug effect can be obtained by oral administration of the NK-inactive+EPO than the NK-active+EPO.

Example 5

Oral Administration of NK+ Ins2 Fusion Polypeptide

To C57BL/6 male mice at 5 weeks of age, 2 mg of STZ (streptozodocin) was peritoneally administered, whereby type 1 diabetic (insulin deficient diabetes) model mice were prepared. The mice at 12 weeks of age and whose blood glucose level after fasting for 3 hours reached about 400 were used. After being fasted for 18 or 24 hours, the mice were given 2 g/kg of glucose load (oral administration of sugar water using a gastric tube). At 30 minutes after the glucose load, the mice were used for study.

To each diabetic mouse, any of the NK-full+Ins2, the NK-active+Ins2, the NK-full alone and the NK-active alone (control) was orally administered in an amount of 5 µg/100 µl. In addition, any of the solutions was intravenously injected in an amount of 5 µg/50 µl via the tail of the mice. Thereafter, the blood glucose level was measured at every 20 minutes, and blood was collected from the heart after 80 minutes or after 120 minutes when a decrease in blood glucose could be confirmed. In addition, in the case of the mice injected intravenously, blood was collected from the heart at 1 hour after the measurement of the blood glucose level. Further, the concentration of Ins2 in the blood of the respective mice was measured by ELISA. The results are as follows.

Figure 8:
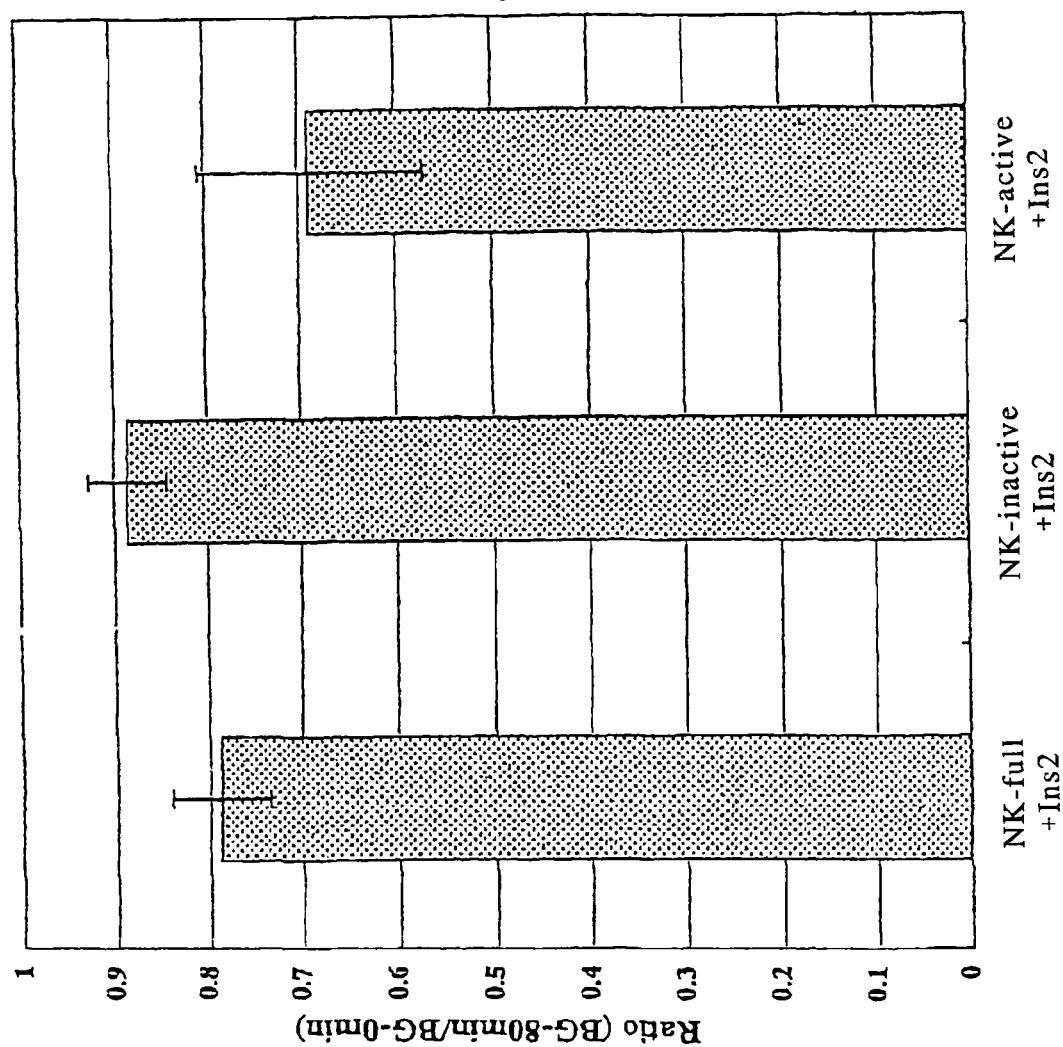
FIG. 8 is a graph showing the effects of oral administration of NK+ Ins2 fusion polypeptide on the blood glucose level of diabetic model mice.
Figure 9:
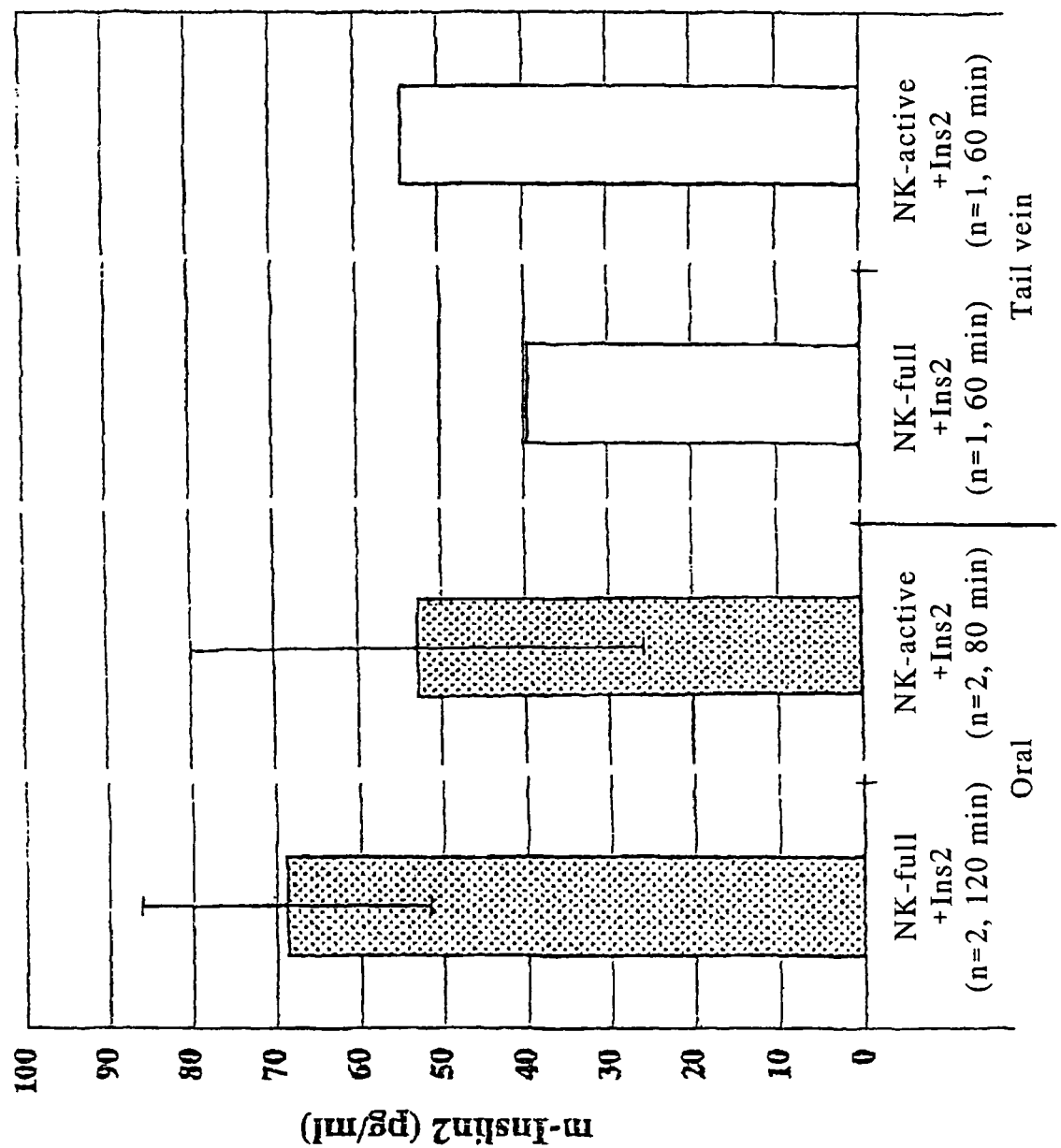
FIG. 9 is a graph showing the effects of oral administration of NK+ Ins2 fusion polypeptide on the Ins2 level in the blood of diabetic model mice.

That is, upon the NK-active+Ins2 and the NK-full, a significant decrease in blood glucose was observed by the oral administration (FIG. 8). Particularly for the NK-active+Ins2, it was confirmed that by the oral administration, the results of a significantly larger decrease in blood glucose level was obtained than by the intravenous injection. Subsequently, the concentration of Ins2 in the blood was measured by an accurate ELISA that enables detection at the level of 10 pg/ml. As a result, in the groups of the NK-full+Ins2 and the NK-active+Ins2, a high concentration of insulin in the blood was observed, and particularly in the case of the NK-full+Ins2, a further higher concentration of insulin was observed by the oral administration as compared with the case of the intravenous injection (FIG. 9).

Example 6

Oral Administration of NK+ G-CSF Fusion Polypeptide (1) Preparation of NK+ G-CSF Fusion Polypeptide A sequence comprising nucleotides 58 to 978 (a polynucleotide encoding the polypeptide from the Met at the 20th position to the Thr at the 326th position of NK: hereinafter also referred to as "the NK-carrier cDNA") of the NK cDNA (SEQ ID NO:1) which had been cloned in Example 1 was prepared.

The NK-carrier cDNA was integrated at the SmaI/BamH site in a pQE-TriSystem His.Strep 1 vector (Qiagen), and a NK-carrier expression vector for *E. coli* was constructed. In addition, a mouse G-CSF cDNA was integrated into the downstream of the NK-carrier cDNA (at the EcoRI/BglII site in the pQE vector), and an NK+ G-CSF expression vector for *E. coli* was prepared. The sequence of the fusion polynucleotide encoding NK+ G-CSF is as shown in SEQ ID NO:6. Incidentally, in SEQ ID NO:6, the nucleotide sequence encoding Ser-Arg-Glu at the 5'-terminus is the sequence at the SmaI site of the pQE vector, and the sequence encoding Gln-Ile-Ser at the 3'-terminus is the sequence at the BglII site of the pQE vector. Further, the sequence encoding Val-Asp-Pro-Asn-Ser at the 311th position to the 315th position is a sequence derived from the pQE vector.

The prepared vector was introduced into an XL 10-Gold Kan Ultracompetent Cell (Stratagene), and the cells were cultured at 37° C. After it was confirmed that the O.D. reached 0.5, IPTG was added to a final concentration of 1 mM, and cultivation was performed at 28° C. for 4 hours. After *E. coli* cells were collected, they were freezed at −80° C., and dissolved in a Lysis buffer. Subsequently, the *E. coli* cells were homogenized with an ultrasonic homogenizer, and separated into soluble components and insoluble components by centrifugation. From the soluble components, a protein with a His tag was purified by HIS-Select Cobalt Affinity Gel (Sigma). After the purification, the eluate was replaced with PBS by using a semipermeable membrane, and endotoxin was removed by using Mustang Membrane (Pall Corporation).

(2) Experimental Groups

Normal BALB/c mice (25 weeks of age, male, purchased from SLC) were allocated to each group with 5 mice, and any of the following samples was administered. Incidentally, in the samples to be administered, BSA (bovine serum albumin) was added to a final concentration of 100 mg/ml. The protein mass in each sample was measured with an optical densitometer using BSA as a control.

The first group: NK+ G-CSF (oral): 16 µg/0.2 ml/mouse 1/1
The second group: NK+ G-CSF (oral): 1.6 µg/0.2 ml/mouse 1/10
The third group: NK+ G-CSF (subcutaneous injection): 16 µg/0.2 ml/mouse 1/1
The fourth group: NK-carrier (oral): 16 µg/0.2 ml/mouse
The fifth group: PBS (subcutaneous injection): 0.2 ml/mouse (3) Experimental Method In the preliminary experiment, it was confirmed that a significant effect is observed over two or more days from the collection of 0.3 ml of blood. Firstly, 0.3 ml of blood was collected from the eye cavity of the BALB/c mice, and the number of white blood cells was counted on the same day. Then, after being fasted for 18 hours, to each mouse, any of the samples above was administered orally using a gastric tube or via a subcutaneous injection. At 24 hours and 48 hours after the administration of the sample, 0.3 ml of blood was collected from the venous sinus of the eye cavity of the mice, and the number of white blood cells was counted immediately. Incidentally, the number of white blood cells was counted at Mitsubishi Chemical BCL.

(4) Results

Figure 10:
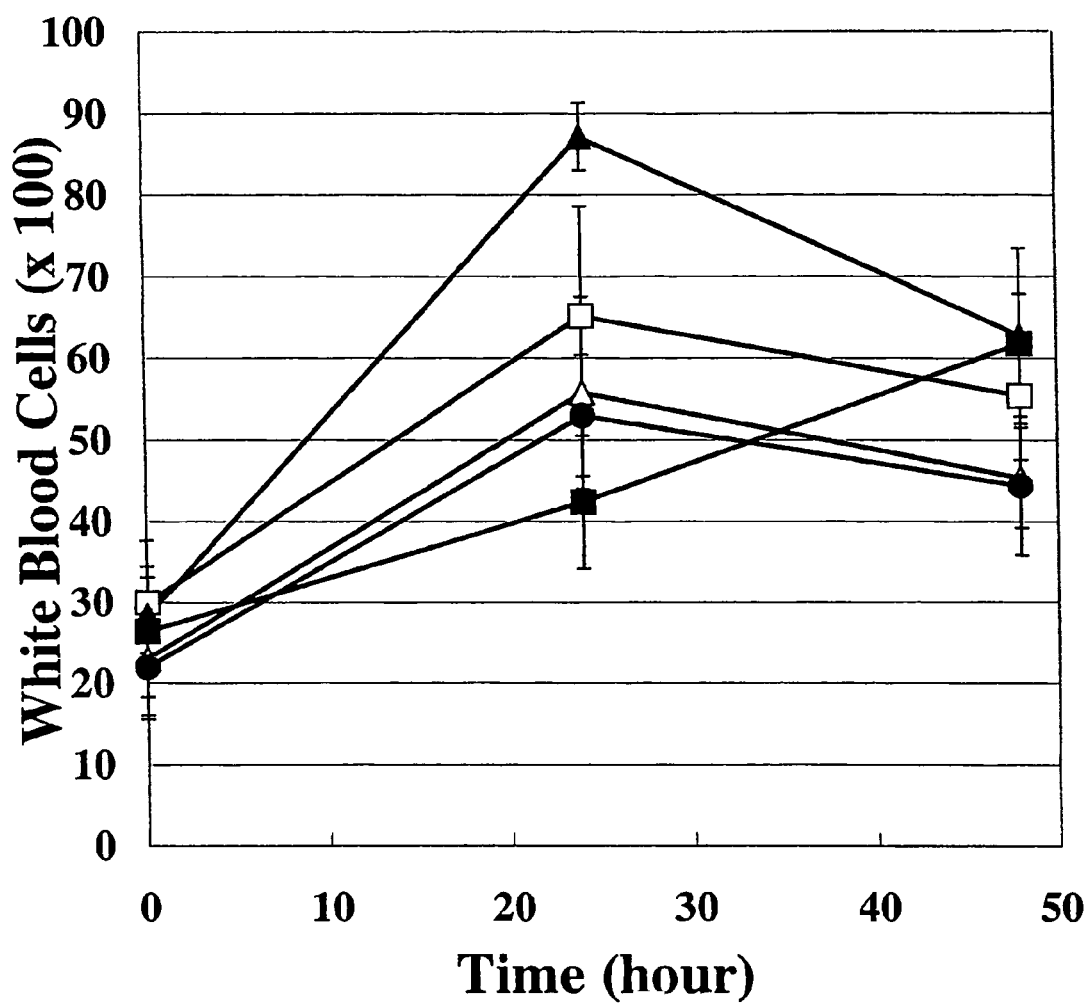
FIG. 10 shows the results of Example 6 and is a graph showing the effects of oral administration of NK+ G-CSF fusion polypeptide on the number of white blood cells in the peripheral blood of mice. In the figure, the vertical axis indicates the number of white blood cells and the horizontal axis indicates the time. The black squares, the white squares, the black triangles, the white triangles and the black circles correspond to the results of oral administration of carrier NK (the fourth group: 5 mice), the results of subcutaneous injection of PBS (the fifth group: 5 mice), the results of oral administration of NK+ G-CSF (the first group: 5 mice), the results of subcutaneous injection of NK+ G-CSF (the third group: 5 mice) and the results of oral administration of NK+ G-CSF (1/10) (the second group: 5 mice), respectively.

The results are as shown in FIG. 10. That is, in the oral administration of NK+ G-CSF (the first group and the second group), a statistically significant effect on an increase in white blood cells could be confirmed at 48 hours after the administration at a dose of 16 μg/mouse (600 μg/kg), however, a significant effect was not observed at a dose of 1.6 μg/mouse (60 μg/kg).

In the subcutaneous injection, even with PBS alone (the fifth group), a significant effect on an increase in white blood cells could be confirmed, though it is smaller compared with the above, possibly due to an effect of blood collection and an immunoreaction with BSA. In the subcutaneous injection of G-CSF (the third group), an increase was observed in four mice out of five, however, the change was small in one mouse, and a significant difference was not observed.

Even in the subcutaneous administration of the NK-carrier (the fourth group), a significant effect on an increase in white blood cells was observed at 24 hours after the administration compared with that at 0 hour.

(5) Discussion

In the group of PBS administration as the control (the fifth group), an increase in white blood cells was observed at 24 and also 48 hours after the administration. In fact, in a single oral administration of NK+ G-CSF (the first and the second groups), there was a tendency of a decrease in white blood cells at 48 hours after the administration instead. It is suggested that there is a possibility that in the case where the concentration of G-CSF is not maintained after G-CSF acts strongly on the bone marrow, white blood cells decrease instead, on the other hand, by the effect of collecting blood in an amount corresponding to about 30% of the total blood amount on consecutive days, the number of white blood cells continues to increase instead.

In the single oral administration of 0.6 mg/kg of NK+ G-CSF, a statistically significant physiological activity could be confirmed at 24 hours after the administration compared with the control, however, in the oral administration of 0.06 mg/kg thereof, a statistically significant physiological activity could not be confirmed. In the single subcutaneous injection of 0.6 mg/kg of NK+ G-CSF, a tendency of an increase was observed, however, a significant increase in white blood cells could not be observed. In the used NK+ G-CSF, the content of G-CSF is about ½, which corresponds to 0.3 mg/kg. For human clinical use, it is generally administered at 50 to 100 mg/head (60 kg) by subcutaneous or intramuscular injection.

These results suggest the possibility that, though G-CSF was orally administered, not only is it absorbed very efficiently through the digestive tract, but also did it not lose the activity in blood. In addition, the possibilities that by subcutaneous injection, individual variability occurs instead, and the conversion into the active form, namely, the conversion from this fusion protein into the active form of G-CSF by the activity of a protease in blood does not always efficiently proceed were suggested. In a case of this fusion polypeptide, a possibility that a polypeptide with high activity can be delivered to a target organ, namely the bone marrow, by rather oral administration was suggested.

In any case, it was confirmed that the possibility of this form of fusion polypeptide as a DDS is very high. It was confirmed that the effect of digestion in the digestive tract is relatively low, and, though it is degraded and metabolized in blood, the concentration that can sufficiently exhibit the activity in the target organ, namely the bone marrow, and the duration of activity were confirmed.

Example 7

Oral Administration of NK+ Insulin Fusion Polypeptide to Diabetic Mice (1) Preparation of NK+ Insulin Fusion Polypeptide The same NK-carrier cDNA as in Example 6 was prepared. The NK-carrier cDNA was integrated at the SmaI/BamH site in a pQE-TriSystem His Strep 1 vector (Qiagen), and a NK-carrier expression vector for E. coli was constructed. In addition, a mouse Insulin 2 cDNA was integrated into the downstream of the NK-carrier cDNA (at the BamHI/EcoRI site in the pQE vector), and an NK+ Insulin expression vector for E. coli was prepared. The sequence of the fusion polynucleotide encoding NK+ Insulin is as shown in SEQ ID NO:8. Incidentally, in SEQ ID NO:8, the nucleotide sequence encoding Ser-Arg-Glu at the 5'-terminus is the sequence at the SmaI site of the pQE vector, and the sequence encoding Pro-Asn-Ser at the 3'-terminus is the sequence at the EcoRI site of the pQE vector. Further, the sequence encoding Val-Asp-Pro at the 311th position to the 313th position is a sequence derived from the pQE vector.

From the constructed vector, NK+ Insulin fusion polypeptide was prepared in the same manner as in Example 6.

(2) Experimental Groups

Normal C57BL/6 mice (6 to 7 weeks of age, male, purchased from SLC) were allocated to each group with 6 to 9 mice, pre-experimental rearing thereof was carried out for 10 days, and 180 mg/kg of STZ was intraperitoneally injected. After about 3 weeks (at 11 weeks of age), the blood glucose level and the blood insulin level were examined, and then any of the following samples was administered. Incidentally, in the samples to be administered, BSA (bovine serum albumin) was added at 100 mg/ml. The protein mass in each sample was measured with an optical densitometer using BSA as a control.

The first group: NK+ Insulin (oral): 40 μg/0.2 ml/mouse 1/1
The second group: NK+ Insulin (oral): 4.0 μg/0.2 ml/mouse 1/10
The third group: NK+ Insulin (subcutaneous injection): 40 μg/0.2 ml/mouse 1/1
The fourth group: NK-carrier (oral): 40 μg/0.2 ml/mouse
The fifth group: PBS (subcutaneous injection): 0.2 ml/mouse
The sixth group: NK+ Insulin (oral): 160 μg/0.2 ml/mouse 1/1
The seventh group: NK+ Insulin (oral): 16 μg/0.2 ml/mouse 1/1
The eighth group: NK-carrier (oral): 160 μg/0.2 ml/mouse (3) Experimental Method The STZ-administered C57BL/6 mice whose blood glucose concentration was about 400 mg/dl after a 3-hour fasting period were fasted for 18 hours, and the fasting blood glucose was measured. Then, glucose (2 g/kg BW) was orally administered using a gastric tube. Each sample was administered after an 18-hour fasting period to the respective mice orally or subcutaneously.

The blood was collected from the venous plexus of the eye cavity of the mice with a capillary, and the blood glucose concentration was measured with GLUTEST ACE (GT-1640, manufactured by Sanwa Kagaku Kenkyusho Co). At 30 minutes after the sugar loading, the blood glucose concentration was measured to confirm that it was increased, and then the sample was administered. Then, at 1, 2 and 4 hours after the administration, measurement of the blood glucose concentration and collection of 0.2 ml of blood were carried out, and the plasma was obtained by centrifugation.

(4) Results

Figure 11:
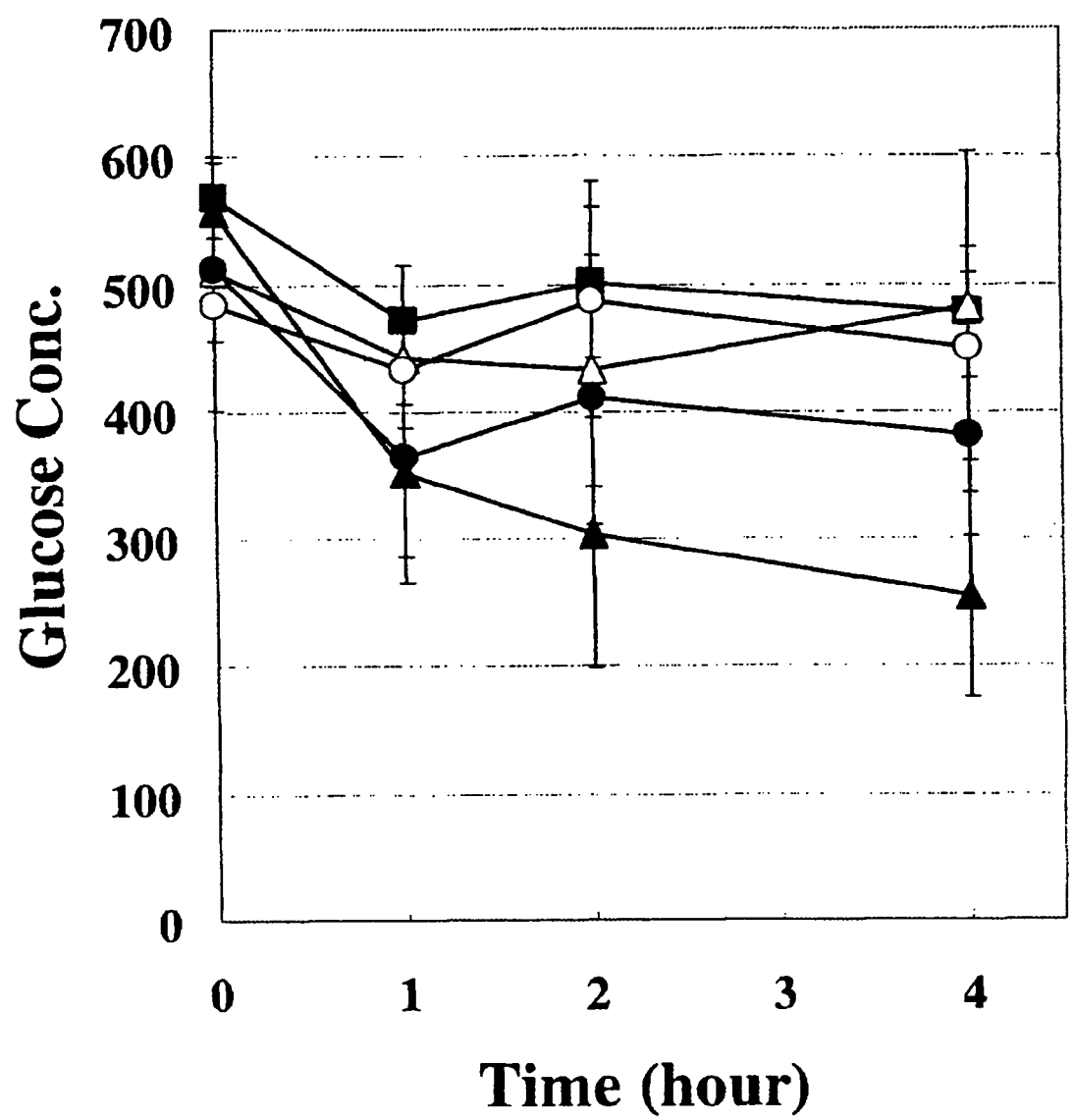
FIG. 11 shows the results of Example 7 and is a graph showing the effects of oral administration of NK+ Insulin fusion polypeptide on the glucose concentration in the blood of diabetic model mice. In the figure, the vertical axis indicates the glucose concentration and the horizontal axis indicates the time. The black squares, the black triangles, the white triangles, the white circles and the black circles correspond to the results of subcutaneous injection of PBS (the fifth group: control: 6 mice), the results of oral administration of NK+ Insulin (the first group: 9 mice), the results of oral administration of NK+ Insulin 2 (1/10) (the second group: 8 mice), the results of oral administration of carrier NK (the fourth group: 8 mice) and the results of subcutaneous injection of NK+ Insulin 2 (the third group), respectively.
Figure 12:
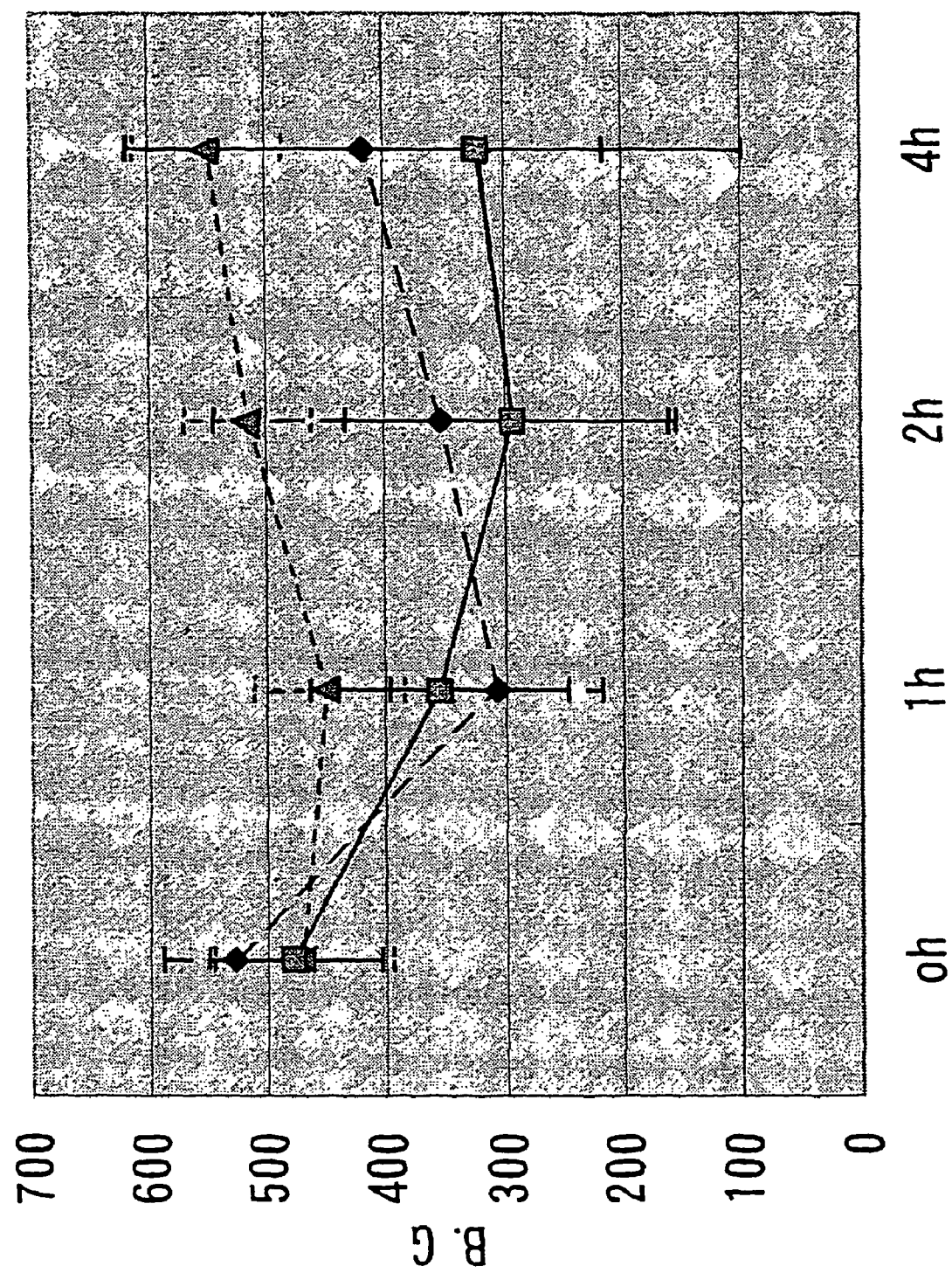
FIG. 12 shows the results of Example 7 and is a graph showing the effects of oral administration of NK+ Insulin fusion polypeptide on the glucose concentration in the blood of diabetic model mice. In the figure, the vertical axis indicates the glucose concentration and the horizontal axis indicates the time. The lozenges, the squares and the triangles correspond to the results of oral administration of NK+ Insulin (the sixth group: 6 mice), the results of oral administration of NK+ Insulin 2 (1/10) (the seventh group: 6 mice) and the results of oral administration of carrier NK (the eighth group: 6 mice), respectively.

The results are as shown in FIGS. 11 and 12. That is, as shown in FIG. 11, in the oral administration of NK+ insulin (the first group and the second group), a statistically significant effect on decreasing blood glucose could be confirmed at a dose of 40 μg/mouse (2.4 mg/kg), however, a significant effect was not observed at a dose of 4.0 μg/mouse (240 μg/kg). Also, in the NK-carrier alone (the fourth group), a tendency of slightly decreasing blood glucose at a dose of 40 μg/mouse (2.4 mg/kg) possibly due to an effect of blood collection and an action of BSA was observed. Incidentally, also in the control (the fifth group), there was a tendency of slightly decreasing blood glucose after the administration.

On the other hand, as shown in FIG. 12, in the oral administration of NK+ Insulin (the sixth group and the seventh group), a statistically significant effect on decreasing blood glucose could be confirmed at a dose of 160 μg/mouse (about 10 mg/kg), however, a significant effect was also observed at a dose of 16.0 μg/mouse (1.0 mg/kg). In the carrier NK alone (the eighth group: 160 μg/mouse (about 10 mg/kg)), a significant change was not observed compared also with the control.

(5) Discussion

In the single oral administration of NK+ Insulin fusion polypeptide at 10, 2.4 and 1.0 mg/kg, a statistically significant effect on decreasing blood glucose could be confirmed, however, in the oral administration at 0.24 mg/kg, a statistically significant physiological activity could not be confirmed. However, in the single oral administration of the carrier NK alone at 10, 2.4 and 0.24 mg/kg, though a slight tendency was observed, a significant effect on decreasing blood glucose could not be observed. In the insulin as the fusion polypeptide used, the content of insulin is about ¼, which corresponds to 2.5, 0.6 and 0.25 mg/kg, respectively. These are a dose which is enough to be applicable to clinical use, and moreover, even at 4 hours after the administration, a significant effect on decreasing blood glucose was maintained. The duration of this effect is superior to that of the effect on decreasing blood glucose by intravenous injection of insulin.

The above results suggest the possibility that, by the oral administration of NK+ Insulin fusion polypeptide, not only is insulin absorbed very efficiently through the digestive tract, but also did it not lose the activity in blood. In a case of this fusion polypeptide, a possibility that a polypeptide with high activity with longer duration can be delivered to a target organ, namely an adipose tissue, muscle, liver or the like, by rather oral administration was suggested.

In any case, it was confirmed that the possibility of this fusion polypeptide as a DDS is very high. It was confirmed that the effect of digestion in the digestive tract is relatively low, and, though it is degraded and metabolized in blood, the concentration that can sufficiently exhibit the activity in the target organ, namely an adipose tissue, muscle, liver or the like, and the duration of activity were confirmed.

Example 8

Blood Kinetics of Insulin by Oral Administration of NK+ Insulin Fusion Polypeptide to Diabetic Mice (1) Preparation of NK+ Insulin Fusion Polypeptide The same NK-carrier cDNA as in Example 6 was prepared. The NK-carrier cDNA was integrated at the BamHI/EcoRI site in a pGEX-5X-3 vector (Amersham Biosciences), and a carrier NK expression vector for *E. coli* was prepared. In addition, a mouse Insulin 2 cDNA was integrated into the downstream of the NK-carrier cDNA (at the RcoRI/SmaI site in the pGEX vector), and an NK+ Insulin expression vector for *E. coli* was prepared. The sequence of the fusion polynucleotide encoding NK+ Insulin fusion polypeptide is as shown in SEQ ID NO:7. Incidentally, in SEQ ID NO:7, the nucleotide sequence encoding Gly-Ile-Pro at the 5'-terminus is the sequence at the BamHI site of the pGEX vector, and the sequence encoding Ser-Arg-Val at the 3'-terminus is the sequence at the SmaI site of the pQE vector. Further, the sequence encoding Arg-Asn-Ser at the 311th position to the 313th position is a sequence derived from the pGEX vector.

From the constructed vector, NK+ Insulin fusion polypeptide was prepared in the same manner as in Example 6. However, this fusion polypeptide was purified by separating a protein with GST tag with GST-Select Affinity Gek (Amarsham Pharmacia) from a soluble component obtained from the homogenized *E. coli* by centrifugation, and removing the GST tag from this protein.

(2) Experimental Groups

Normal C57BL/6 mice (6 to 7 weeks of age, male, purchased from SLC) were allocated to each group with 5 to 8 mice, pre-experimental rearing thereof was carried out for 10 days, and 180 mg/kg of STZ was intraperitoneally injected. After about 3 weeks (at 11 weeks of age), the blood glucose level and the blood insulin level were examined, and then any of the following samples was administered. Incidentally, in the NK+ Insulin sample, components purified from a medium of a protein preparation kit is contained.

The first group: NK+ Insulin (oral): 20 μg/0.1 ml/mouse 1/1
The second group: NK+ Insulin (subcutaneous injection): 20 μg/0.1 ml/mouse 1/1
The third group: PBS (subcutaneous injection): 0.1 ml/mouse, 0.5 ml/mouse (3) Experimental Method The STZ-administered C57BL/6 mice whose blood glucose concentration was about 400 mg/dl after a 3-hour fasting period were fasted for 18 hours, and the fasting blood glucose was measured. Then, glucose (2 g/kg BW) was orally administered using a gastric tube. Each sample was administered after the 18-hour fasting period to the respective mice orally or subcutaneously.

The blood was collected from the venous plexus of the eye cavity of the mice with a capillary, and the blood glucose concentration was measured with GLUTEST ACE (GT-1640, manufactured by Sanwa Kagaku Kenkyusho Co). At 30 minutes after the sugar loading, the blood glucose concentration was measured to confirm that it was increased, and then the sample was administered. Then, immediately thereafter (actually, at about 5 minutes thereafter), and at 25, 50 and 80 minutes after the administration, 0.2 ml of blood was collected, and the plasma was obtained by centrifugation. By using the obtained plasma, ELISA was carried out for insulin, and blood concentration was calculated.

(4) Results

Figure 13:
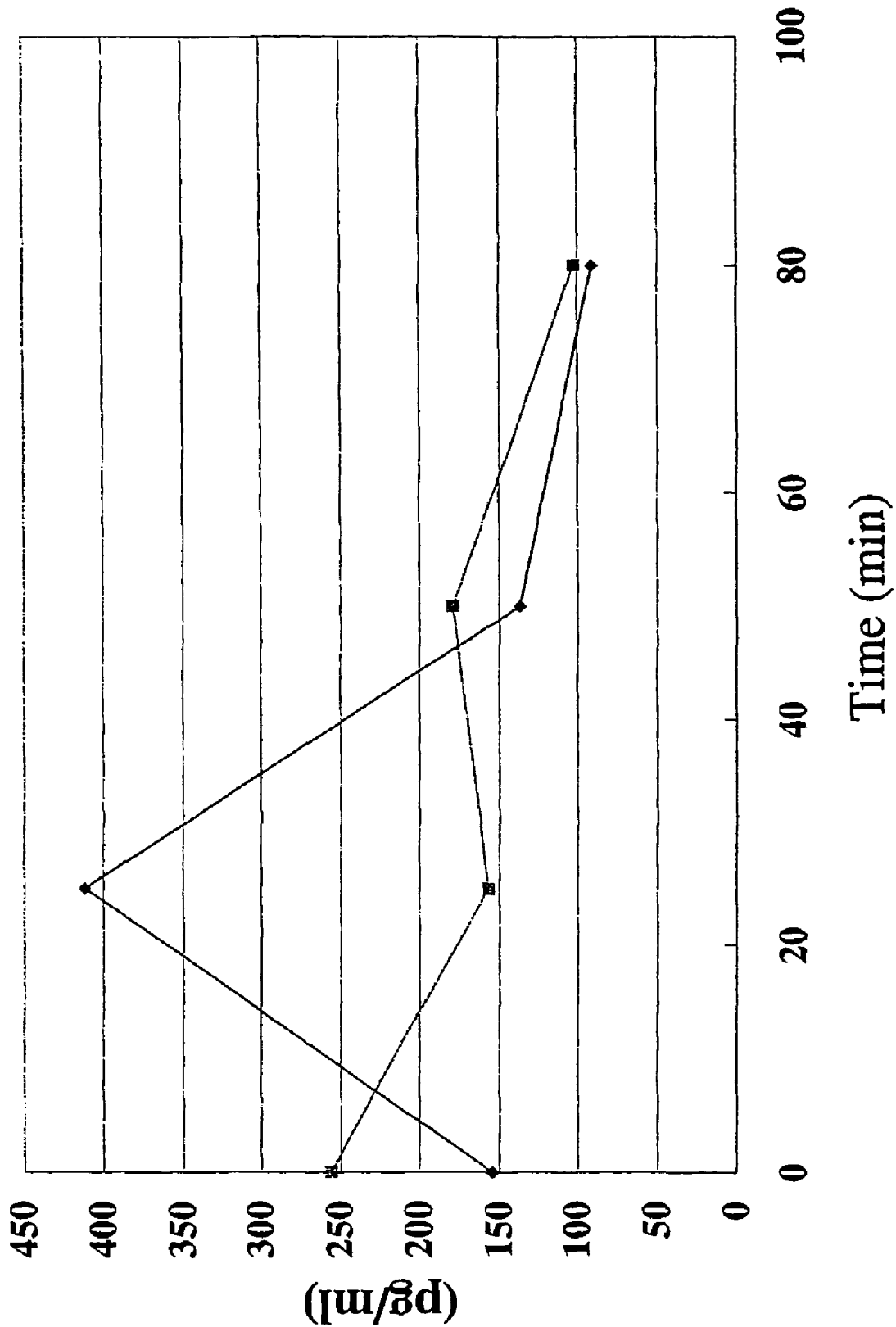
FIG. 13 shows the results of Example 8 and is a graph showing the effects of oral administration of NK+ Insulin fusion polypeptide on the insulin concentration in the blood of diabetic model mice. In the figure, the vertical axis indicates the insulin concentration in the blood and the horizontal axis indicates the time (min). The lozenges and the squares correspond to the results of oral administration of NK+ Insulin (the first group: 4 mice) and the results of subcutaneous injection of NK+ Insulin 2 (the second group: 3 mice), respectively.

The results are as shown in FIG. 13. That is, in the oral administration of NK+ insulin (the first group), a statistically significant insulin induction was observed after the administration at a dose of 20 μg/mouse (1.2 mg/kg) compared with the control, namely PBS alone (the third group). Also in the subcutaneous administration of the same (the second group), a statistically significant insulin induction was observed after the administration at a dose of 20 μg/mouse (1.2 mg/kg) of NK-Insulin. Incidentally, the blood insulin level in the PBS subcutaneous injection (the third group), which is not shown in FIG. 13, was 24 pg/ml or lower in any individual.

(5) Discussion

It was confirmed that in the single oral or subcutaneous administration of 1.2 mg/kg of NK+ Insulin fusion polypeptide, a statistically significant insulin level in blood was maintained. In the fusion polypeptide used, the content of insulin is about ¼, which corresponds to 0.3 mg/kg. This is a dose which is enough to be applicable to clinical use, and moreover, even at 4 hours after the administration, a significant blood insulin level was maintained. The duration of this effect is superior to that of the effect on decreasing blood glucose by subcutaneous injection of insulin. In addition, also a change of the concentration in blood was by no means inferior compared with the subcutaneous injection at the same dose as the oral administration.

However, even in the case of subcutaneous injection, the maximum blood concentration after the administration at 1.2 mg/kg was 0.4 ng/ml even on an average, therefore it is suggested that if the concentration of insulin can be maintained even at a relatively low concentration (1.0 ng/ml or lower), the blood glucose will be decreased.

The above results suggest the possibility that, by the oral administration of NK+ Insulin fusion polypeptide, not only is insulin absorbed very efficiently through the digestive tract, but also did it not lose the activity in blood. In a case of this fusion polypeptide, a possibility that a polypeptide with high activity with longer duration can be delivered to a target organ, namely an adipose tissue, muscle, liver or the like, by rather oral administration was suggested.

In any case, it was confirmed that the possibility of this fusion polypeptide as a DDS is very high. It was confirmed that the effect of digestion in the digestive tract is relatively low, and, though it is degraded and metabolized in blood, the concentration that can sufficiently exhibit the activity in the target organ, namely an adipose tissue, muscle, liver or the like, and the duration of activity are retained.

Example 9

Oral Administration of NK+ Adiponectin (1) Preparation of Fusion Polypeptide

The same NK-carrier cDNA as in Example 6 was prepared. The NK-carrier cDNA was integrated at the SmaI/BamH site in a pQE-TriSystem His.Strep 1 vector (Qiagen), and a NK-carrier expression vector for *E. coli* was constructed. In addition, a mouse adiponectin cDNA was integrated into the downstream of the carrier NK cDNA (at the BamHI/EcoRI site in the pQE vector), and an NK+ Adiponectin expression vector for *E. coli* was prepared. The sequence of the fusion polynucleotide encoding NK+ Adiponectin is as shown in SEQ ID NO:9. Incidentally, in SEQ ID NO:9, the nucleotide sequence encoding Ser-Arg-Glu at the 5'-terminus is the sequence at the SmaI site of the pQE vector, and the sequence encoding Asp-Pro-Asn-Ser at the 3'-terminus is the sequence at the EcoRI site of the pQE vector. Further, the sequence encoding Val-Asp-Pro at the 311th position to the 313th position is a sequence derived from the pQE vector. From the constructed vector, NK+ Adiponectin fusion polypeptide was prepared in the same manner as in Example 6.

(2) Experimental Groups

C57BL db/db mice (6 weeks of age, male, purchased from CLEA) were allocated to each group with 4 mice, pre-experimental rearing thereof was carried out for 4 weeks, and the blood glucose concentration after fasting at 10 weeks of age was examined. Then, any of the following samples was administered. Incidentally, in the samples to be administered, BSA (bovine serum albumin) was added at 100 mg/ml. The protein mass in each sample was measured with an optical densitometer using BSA as a control.

The first group: NK+ Adiponectin (oral): 25 µg/0.2 ml/mouse 1/1
The second group: NK+ Adiponectin (oral): 2.5 µg/0.2 ml/mouse 1/10
The third group: Adiponectin (oral): 25 µg/0.2 ml/mouse 1/1
The fourth group: NK-carrier (oral): 25 µg/0.2 ml/mouse
(3) Experimental Method
(3-1) Preliminary Study By using the above-mentioned C57BL db/db mice at 8 weeks of age whose blood glucose concentration was about 400 mg/ml, measurement of blood glucose and collection of blood were carried out after a 3-hour fasting period. At the time when fasting was continued to 18 hours, the first administration of the sample was carried out. Also on the next day and the day after, administration of the sample was carried out at the same time of day, and the effect of the three administrations in total were examined by measuring the blood glucose concentration after a 3-hour fasting period again.

(3-2) Time Course Study after Administration

After finishing examining the change in blood glucose as described above, the C57BL db/db mice were fasted for 18 hours, and the fasting blood glucose was measured. Then, glucose (2 g/kg BW) was orally administered using a gastric tube. Each sample was administered after an 18-hour fasting period to the respective mice orally or subcutaneously.

The blood was collected from the eye or the venous plexus of the mice with a capillary, and the blood glucose concentration was measured with GLUTEST ACE (GT-1640, manufactured by Sanwa Kagaku Kenkyusho Co). At 30 minutes after the sugar loading, the blood glucose concentration was measured to confirm that it was increased, and then the synthesized protein was administered. Then, at 1, 2 and 4 hours after the administration, measurement of the blood glucose concentration was carried out.

(4) Results

Figure 14:
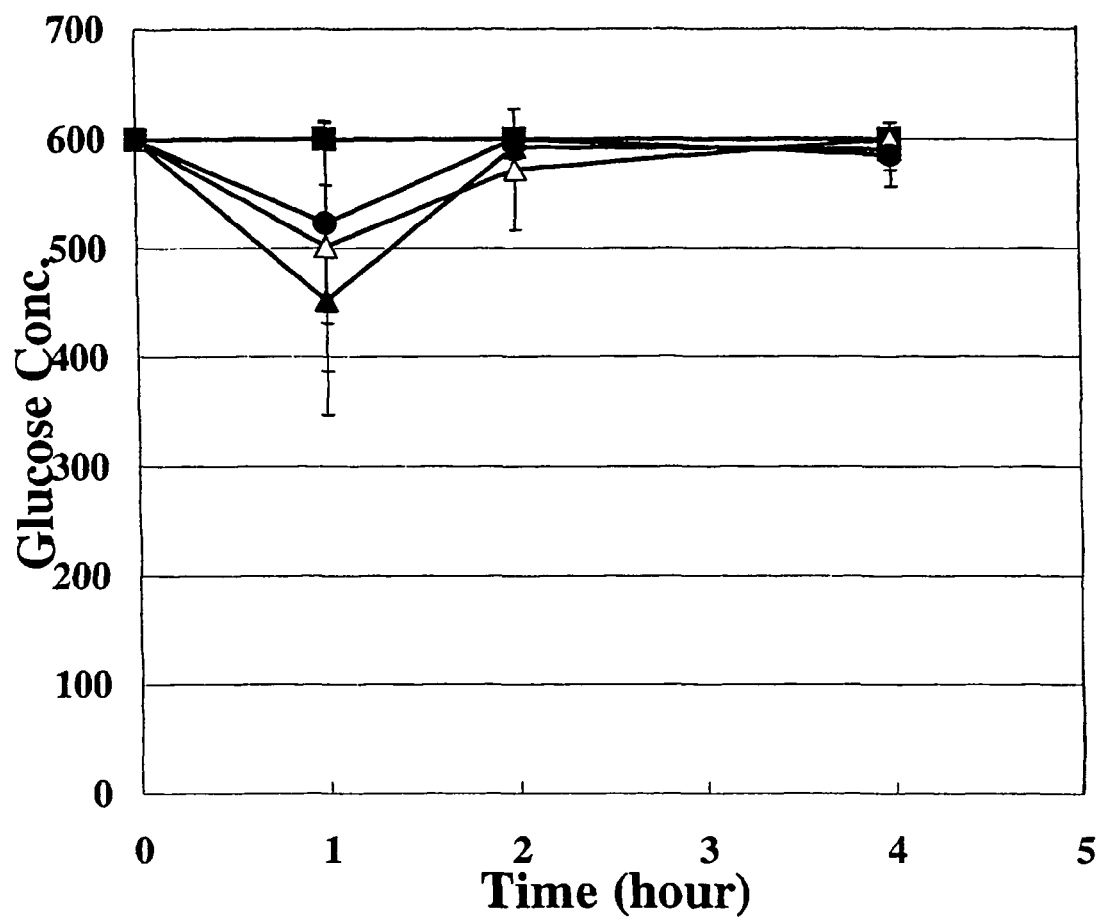
FIG. 14 shows the results of Example 9 and is a graph showing the effects of oral administration of NK+ Adiponectin fusion polypeptide on the glucose concentration in the blood of diabetic model mice. In the figure, the vertical axis indicates the glucose concentration and the horizontal axis indicates the time. The black squares, the black triangles, the white triangles, and the black circles correspond to the results of oral administration of adiponectin (the third group: 4 mice), the results of oral administration of NK+ Adiponectin (the first group: 4 mice), the results of oral administration of NK+ Adiponectin (1/10) (the second group: 4 mice) and the results of oral administration of carrier NK (the fourth group: 4 mice), respectively.

The results are as shown in FIG. 14. In the time course observation study after the oral administration, a statistically significant effect on decreasing blood glucose could be confirmed at a dose of 25 µg/mouse (625 µg/kg) of NK+ Adiponectin (the first group), however, a significant effect was not observed at a dose of 2.5 µg/mouse (62.5 µg/kg) (the second group). In addition, also in the carrier NK alone (the fourth group), there was a tendency of slightly decreasing blood glucose at a dose of 20 µg/mouse (500 µg/kg) possibly due to an effect of blood collection and an action of BSA was observed, though there was not a statistical significance. Further, also in the control (the fourth group), there was a tendency of slightly decreasing blood glucose after the administration.

(5) Discussion

In the oral administration of 0.625 mg/kg of NK+ Adiponectin fusion polypeptide, a statistically significant effect on decreasing blood glucose could be confirmed at 1 hour after the fourth administration, however, a statistically significant physiological effect could not be confirmed in the oral administration of 62.5 µg/kg, which is 1/10 of the above amount. In addition, in the single oral administration of the NK-carrier alone at 500 µg/kg, though a slight tendency was observed, a significant effect on decreasing blood glucose could not be observed. In the fusion polypeptide used, the content of adiponectin is about ½, which corresponds to about 300 µg/kg. This is a dose which is more than enough to be applicable to clinical use. It is considered that the meaning of suppressing the increase in blood glucose immediately after eating is not small.

In any case, it was confirmed that the possibility of this fusion polypeptide as a DDS is very high. It was confirmed that the effect of digestion in the digestive tract is relatively low, and the concentration that can sufficiently exhibit the activity in the target organ, namely an adipose tissue, muscle, liver or the like was confirmed. However, the type 2 diabetic model animal, C57BL db/db mice in this case have just reached 10 weeks of age, and it is considered that the symptom was relatively mild. In particular, it is said that 95% of the patients suffering from diabetes in Japan are patients with type 2 diabetes cased by insulin resistance. It is said that adiponenctin has a special effect on this type 2 diabetes, and it is known that it has an improving effect on insulin resistance. The meaning that the possibility of its oral administration as well as its physiological activities was shown is extremely large.

INDUSTRIAL APPLICABILITY

According to the present invention, by orally administering a bioactive polypeptide, which is effective on treating a disease, in vivo administration thereof becomes possible. In addition, it has a great meaning that the migration rate into the blood is high as a result that it is difficult to be digested and degraded and easy to be absorbed. Not only does it increase the possibility of applying a novel useful protein, but also does it result in energy saving by eliminating medical care cost, reducing waste disposal cost or the like, and further, it can make the risk of releasing the active protein remaining in the container for injection, namely syringe, to nature small.

In addition, by considering the migration rate into the blood or the efficacy, this invention has a great meaning in the industry, for example, the possibility that the disease state of target organ varies depending on the amino acid sequence of the polypeptide absorbable into digestive organs is high, including the fact that there is a possibility as a completely novel DDS.

The invention claimed is:

1. A method for in vivo testing of a toxicity of a substance that is not absorbable through a digestive organ of an animal, comprising:

orally administering a complex of a polypeptide comprising at least a 100 consecutive amino acid sequence selected from the 1st to 362nd amino acid of SEQ ID NO: 2, which assists absorption of a substance into the digestive organ when the substance and the polypeptide are orally taken, wherein the polypeptide comprises no more than 362 amino acids of SEQ ID NO: 2 and a substance, which is not absorbable by itself through a digestive organ of an animal, to an animal, and assessing damage to the animal to thereby determine the toxicity of the substance to the animal.

2. A method for administering a bioactive peptide which is not absorbable by itself through a digestive organ of an animal, comprising administering the bioactive polypeptide together with a polypeptide having the amino acid sequence of SEQ ID NO: 2 or a polypeptide having at least a 100 consecutive amino acid sequence selected from the 1st to 362nd amino acid of SEQ ID NO: 2 wherein the peptide comprises no more than 362 amino acids of SEQ ID NO: 2.

* * * * *

SEQUENCE LISTING

```
<160> NUMBER OF SEQ ID NOS: 9

<210> SEQ ID NO 1
<211> LENGTH: 1146
<212> TYPE: DNA
<213> ORGANISM: Bacillus subtilis
<220> FEATURE:
<221> NAME/KEY: CDS
<222> LOCATION: (1)..(1146)
<223> OTHER INFORMATION:
<300> PUBLICATION INFORMATION:
<308> DATABASE ACCESSION NUMBER: GenBank/AY219901
<309> DATABASE ENTRY DATE: 2003-03-23
<313> RELEVANT RESIDUES: (1)..(1146)

<400> SEQUENCE: 1 atg aga agc aaa aaa ttg tgg atc agc ttg ttg ttt gcg tta acg tta      48
Met Arg Ser Lys Lys Leu Trp Ile Ser Leu Leu Phe Ala Leu Thr Leu
1               5                   10                  15 atc ttt acg atg gcg ttc agc aac atg tct gcg cag gct gcc gga aaa      96
Ile Phe Thr Met Ala Phe Ser Asn Met Ser Ala Gln Ala Ala Gly Lys
                20                  25                  30 agc agt aca gaa aag aaa tac att gtc gga ttt aag cag aca atg agt     144
Ser Ser Thr Glu Lys Lys Tyr Ile Val Gly Phe Lys Gln Thr Met Ser
            35                  40                  45 gcc atg agt tcc gcc aag aaa aag gat gtt att tct gaa aaa ggc gga     192
Ala Met Ser Ser Ala Lys Lys Lys Asp Val Ile Ser Glu Lys Gly Gly
        50                  55                  60 aag gtt caa aag caa ttt aag tat gtt aac gcg gcc gca gca aca ttg     240
Lys Val Gln Lys Gln Phe Lys Tyr Val Asn Ala Ala Ala Ala Thr Leu
65                  70                  75                  80 gat gaa aaa gct gta aaa gaa ttg aaa aaa gat ccg agc gtt gca tat     288
Asp Glu Lys Ala Val Lys Glu Leu Lys Lys Asp Pro Ser Val Ala Tyr
                85                  90                  95 gtg gaa gaa gat cat att gca cat gaa tat gcg caa tct gtt cct tat     336
Val Glu Glu Asp His Ile Ala His Glu Tyr Ala Gln Ser Val Pro Tyr
                100                 105                 110 ggc att tct caa att aaa gcg ccg gct ctt cac tct caa ggc tac aca     384
Gly Ile Ser Gln Ile Lys Ala Pro Ala Leu His Ser Gln Gly Tyr Thr
            115                 120                 125 ggc tct aac gta aaa gta gct gtt atc gac agc gga att gac tct tct     432
Gly Ser Asn Val Lys Val Ala Val Ile Asp Ser Gly Ile Asp Ser Ser
        130                 135                 140 cat cct gac tta aac gtc aga ggc gga gca agc ttc gtt cct tct gaa     480
His Pro Asp Leu Asn Val Arg Gly Gly Ala Ser Phe Val Pro Ser Glu
145                 150                 155                 160 aca aac cca tac cag gac ggc agt tct cac ggt acg cat gtc gcc ggt     528
Thr Asn Pro Tyr Gln Asp Gly Ser Ser His Gly Thr His Val Ala Gly
```

```
                        165                 170                 175
acg att gcc gct ctt aat aac tca atc ggt gtt ctg ggc gta gcg cca      576
Thr Ile Ala Ala Leu Asn Asn Ser Ile Gly Val Leu Gly Val Ala Pro
            180                 185                 190 agc gca tca tta tat gca gta aaa gtg ctt gat tca aca gga agc ggc      624
Ser Ala Ser Leu Tyr Ala Val Lys Val Leu Asp Ser Thr Gly Ser Gly
            195                 200                 205 caa tat agc tgg att att aac ggc att gag tgg gcc att tcc aac aat      672
Gln Tyr Ser Trp Ile Ile Asn Gly Ile Glu Trp Ala Ile Ser Asn Asn
            210                 215                 220 atg gat gtt atc aac atg agc ctt ggc gga cct act ggt tct aca gcg      720
Met Asp Val Ile Asn Met Ser Leu Gly Gly Pro Thr Gly Ser Thr Ala
225                 230                 235                 240 ctg aaa aca gta gtt gat aaa gcg gtt tcc agc ggt atc gtc gtt gct      768
Leu Lys Thr Val Val Asp Lys Ala Val Ser Ser Gly Ile Val Val Ala
            245                 250                 255 gcc gca gcc gga aac gaa ggt tca tcc gga agc aca agc aca gtc ggc      816
Ala Ala Ala Gly Asn Glu Gly Ser Ser Gly Ser Thr Ser Thr Val Gly
            260                 265                 270 tac cct gca aaa tat cct tct act att gca gta ggt gcg gta aac agc      864
Tyr Pro Ala Lys Tyr Pro Ser Thr Ile Ala Val Gly Ala Val Asn Ser
            275                 280                 285 agc aac caa aga gct tca ttc tcc agc gta ggt tct gag ctt gat gta      912
Ser Asn Gln Arg Ala Ser Phe Ser Ser Val Gly Ser Glu Leu Asp Val
            290                 295                 300 atg gct cct ggc gtg tcc atc caa agc aca ctt cct gga ggc act tac      960
Met Ala Pro Gly Val Ser Ile Gln Ser Thr Leu Pro Gly Gly Thr Tyr
305                 310                 315                 320 ggc gct tat aac gga acg tcc atg gcg act cct cac gtt gcc gga gca     1008
Gly Ala Tyr Asn Gly Thr Ser Met Ala Thr Pro His Val Ala Gly Ala
            325                 330                 335 gca gcg cta att ctt tct aag cac ccg act tgg aca aac gcg caa gtc     1056
Ala Ala Leu Ile Leu Ser Lys His Pro Thr Trp Thr Asn Ala Gln Val
            340                 345                 350 cgt gat cgt tta gaa agc act gca aca tac ctt gga agc tct ttc tac     1104
Arg Asp Arg Leu Glu Ser Thr Ala Thr Tyr Leu Gly Ser Ser Phe Tyr
            355                 360                 365 tat gga aaa ggg tta atc aac gta caa gca gct gca caa taa              1146
Tyr Gly Lys Gly Leu Ile Asn Val Gln Ala Ala Ala Gln
            370                 375                 380

<210> SEQ ID NO 2
<211> LENGTH: 381
<212> TYPE: PRT
<213> ORGANISM: Bacillus subtilis

<400> SEQUENCE: 2

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
                20                  25                  30

Ser Ser Thr Glu Lys Lys Tyr Ile Val Gly Phe Lys Gln Thr Met Ser
            35                  40                  45

Ala Met Ser Ser Ala Lys Lys Lys Asp Val Ile Ser Glu Lys Gly Gly
        50                  55                  60

Lys Val Gln Lys Gln Phe Lys Tyr Val Asn Ala Ala Ala Ala Thr Leu
65                  70                  75                  80

Asp Glu Lys Ala Val Lys Glu Leu Lys Lys Asp Pro Ser Val Ala Tyr
                85                  90                  95
```

```
Val Glu Glu Asp His Ile Ala His Glu Tyr Ala Gln Ser Val Pro Tyr
            100                 105                 110

Gly Ile Ser Gln Ile Lys Ala Pro Ala Leu His Ser Gln Gly Tyr Thr
        115                 120                 125

Gly Ser Asn Val Lys Val Ala Val Ile Asp Ser Gly Ile Asp Ser Ser
    130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ala Pro
            180                 185                 190

Ser Ala Ser Leu Tyr Ala Val Lys Val Leu Asp Ser Thr Gly Ser Gly
        195                 200                 205

Gln Tyr Ser Trp Ile Ile Asn Gly Ile Glu Trp Ala Ile Ser Asn Asn
    210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
            260                 265                 270

Tyr Pro Ala Lys Tyr Pro Ser Thr Ile Ala Val Gly Ala Val Asn Ser
        275                 280                 285

Ser Asn Gln Arg Ala Ser Phe Ser Ser Val Gly Ser Glu Leu Asp Val
    290                 295                 300

Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Gly Ala
                325                 330                 335

Ala Ala Leu Ile Leu Ser Lys His Pro Thr Trp Thr Asn Ala Gln Val
            340                 345                 350

Arg Asp Arg Leu Glu Ser Thr Ala Thr Tyr Leu Gly Ser Ser Phe Tyr
        355                 360                 365

Tyr Gly Lys Gly Leu Ile Asn Val Gln Ala Ala Ala Gln
    370                 375                 380

<210> SEQ ID NO 3
<211> LENGTH: 537
<212> TYPE: DNA
<213> ORGANISM: Mus musculus
<220> FEATURE:
<221> NAME/KEY: CDS
<222> LOCATION: (1)..(537)
<223> OTHER INFORMATION:
<300> PUBLICATION INFORMATION:
<308> DATABASE ACCESSION NUMBER: GenBank/M13926
<309> DATABASE ENTRY DATE: 1993-06-12
<313> RELEVANT RESIDUES: (1)..(534)

<400> SEQUENCE: 3 gtt ccc ctg gtc act gtc agc gct ctg cca cca tcc ctg cct ctg ccc    48
Val Pro Leu Val Thr Val Ser Ala Leu Pro Pro Ser Leu Pro Leu Pro
1               5                   10                  15 cga agc ttc ctg ctt aag tcc ctg gag caa gtg agg aag atc cag gcc    96
Arg Ser Phe Leu Leu Lys Ser Leu Glu Gln Val Arg Lys Ile Gln Ala
                20                  25                  30 agc ggc tcg gtg ctg ctg gag cag ttg tgt gcc acc tac aag ctg tgt   144
Ser Gly Ser Val Leu Leu Glu Gln Leu Cys Ala Thr Tyr Lys Leu Cys
```

```
cac ccc gag gag ctg gtg ttg ctg ggc cac tct ctg ggg atc ccg aag       192
His Pro Glu Glu Leu Val Leu Leu Gly His Ser Leu Gly Ile Pro Lys
 50                  55                  60 gct tcc ctg agt ggc tgc tct agc cag gcc ctg cag cag aca cag tgc       240
Ala Ser Leu Ser Gly Cys Ser Ser Gln Ala Leu Gln Gln Thr Gln Cys
 65                  70                  75                  80 cta agc cag ctc cac agt ggg ctc tgc ctc tac caa ggt ctc ctg cag       288
Leu Ser Gln Leu His Ser Gly Leu Cys Leu Tyr Gln Gly Leu Leu Gln
                 85                  90                  95 gct cta tcg ggt att tcc cct gcc ctg gcc ccc acc ttg gac ttg ctt       336
Ala Leu Ser Gly Ile Ser Pro Ala Leu Ala Pro Thr Leu Asp Leu Leu
            100                 105                 110 cag ctg gat gtt gcc aac ttt gcc acc acc atc tgg cag cag atg gaa       384
Gln Leu Asp Val Ala Asn Phe Ala Thr Thr Ile Trp Gln Gln Met Glu
        115                 120                 125 aac cta ggg gtg gcc cct act gtg cag ccc aca cag agc gcc atg cca       432
Asn Leu Gly Val Ala Pro Thr Val Gln Pro Thr Gln Ser Ala Met Pro
130                 135                 140 gcc ttc act tct gcc ttc cag cgc cgg gca gga ggt gtc ctg gcc att       480
Ala Phe Thr Ser Ala Phe Gln Arg Arg Ala Gly Gly Val Leu Ala Ile
145                 150                 155                 160 tcg tac ctg cag ggc ttc ctg gag acg gct cgc ctt gct ctg cac cac       528
Ser Tyr Leu Gln Gly Phe Leu Glu Thr Ala Arg Leu Ala Leu His His
                165                 170                 175 ttg gcc tag                                                           537
Leu Ala <210> SEQ ID NO 4
<211> LENGTH: 333
<212> TYPE: DNA
<213> ORGANISM: Mus musculus
<220> FEATURE:
<221> NAME/KEY: CDS
<222> LOCATION: (1)..(333)
<223> OTHER INFORMATION:
<300> PUBLICATION INFORMATION:
<308> DATABASE ACCESSION NUMBER: GenBank/NM_008387
<309> DATABASE ENTRY DATE: 2003-04-07
<313> RELEVANT RESIDUES: (1)..(333)

<400> SEQUENCE: 4 atg gcc ctg tgg atg cgc ttc ctg ccc ctg ctg gcc ctg ctc ttc ctc        48
Met Ala Leu Trp Met Arg Phe Leu Pro Leu Leu Ala Leu Leu Phe Leu
 1               5                  10                  15 tgg gag tcc cac ccc acc cag gct ttt gtc aag cag cac ctt tgt ggt        96
Trp Glu Ser His Pro Thr Gln Ala Phe Val Lys Gln His Leu Cys Gly
                20                  25                  30 tcc cac ctg gtg gag gct ctc tac ctg gtg tgt ggg gag cgt ggc ttc       144
Ser His Leu Val Glu Ala Leu Tyr Leu Val Cys Gly Glu Arg Gly Phe
            35                  40                  45 ttc tac aca ccc atg tcc cgc cgt gaa gtg gag gac cca caa gtg gca       192
Phe Tyr Thr Pro Met Ser Arg Arg Glu Val Glu Asp Pro Gln Val Ala
 50                  55                  60 caa ctg gag ctg ggt gga ggc ccg gga gca ggt gac ctt cag acc ttg       240
Gln Leu Glu Leu Gly Gly Gly Pro Gly Ala Gly Asp Leu Gln Thr Leu
 65                  70                  75                  80 gca ctg gag gtg gcc cag cag aag cgt ggc att gta gat cag tgc tgc       288
Ala Leu Glu Val Ala Gln Gln Lys Arg Gly Ile Val Asp Gln Cys Cys
                 85                  90                  95 acc agc atc tgc tcc ctc tac cag ctg gag aac tac tgc aac tag           333
Thr Ser Ile Cys Ser Leu Tyr Gln Leu Glu Asn Tyr Cys Asn
            100                 105                 110
```

<210> SEQ ID NO 5
<211> LENGTH: 579
<212> TYPE: DNA
<213> ORGANISM: Mus musculus
<220> FEATURE:
<221> NAME/KEY: CDS
<222> LOCATION: (1)..(579)
<223> OTHER INFORMATION:
<300> PUBLICATION INFORMATION:
<308> DATABASE ACCESSION NUMBER: GenBank/NM_007942
<309> DATABASE ENTRY DATE: 2003-04-06
<313> RELEVANT RESIDUES: (1)..(579)

<400> SEQUENCE: 5

```
atg ggg gtg ccc gaa cgt ccc acc ctg ctg ctt tta ctc tcc ttg cta      48
Met Gly Val Pro Glu Arg Pro Thr Leu Leu Leu Leu Leu Ser Leu Leu
1               5                   10                  15 ctg att cct ctg ggc ctc cca gtc ctc tgt gct ccc cca cgc ctc atc      96
Leu Ile Pro Leu Gly Leu Pro Val Leu Cys Ala Pro Pro Arg Leu Ile
            20                  25                  30 tgc gac agt cga gtt ctg gag agg tac atc tta gag gcc aag gag gca     144
Cys Asp Ser Arg Val Leu Glu Arg Tyr Ile Leu Glu Ala Lys Glu Ala
        35                  40                  45 gaa aat gtc acg atg ggt tgt gca gaa ggt ccc aga ctg agt gaa aat     192
Glu Asn Val Thr Met Gly Cys Ala Glu Gly Pro Arg Leu Ser Glu Asn
    50                  55                  60 att aca gtc cca gat acc aaa gtc aac ttc tat gct tgg aaa aga atg     240
Ile Thr Val Pro Asp Thr Lys Val Asn Phe Tyr Ala Trp Lys Arg Met
65                  70                  75                  80 gag gtg gaa gaa cag gcc ata gaa gtt tgg caa ggc ctg tcc ctg ctc     288
Glu Val Glu Glu Gln Ala Ile Glu Val Trp Gln Gly Leu Ser Leu Leu
                85                  90                  95 tca gaa gcc atc ctg cag gcc cag gcc ctg cta gcc aat tcc tcc cag     336
Ser Glu Ala Ile Leu Gln Ala Gln Ala Leu Leu Ala Asn Ser Ser Gln
            100                 105                 110 cca cca gag acc ctt cag ctt cat ata gac aaa gcc atc agt ggt cta     384
Pro Pro Glu Thr Leu Gln Leu His Ile Asp Lys Ala Ile Ser Gly Leu
        115                 120                 125 cgt agc ctc act tca ctg ctt cgg gta ctg gga gct cag aag gaa ttg     432
Arg Ser Leu Thr Ser Leu Leu Arg Val Leu Gly Ala Gln Lys Glu Leu
    130                 135                 140 atg tcg cct cca gat acc acc cca cct gct cca ctc cga aca ctc aca     480
Met Ser Pro Pro Asp Thr Thr Pro Pro Ala Pro Leu Arg Thr Leu Thr
145                 150                 155                 160 gtg gat act ttc tgc aag ctc ttc cgg gtc tac gcc aac ttc ctc cgg     528
Val Asp Thr Phe Cys Lys Leu Phe Arg Val Tyr Ala Asn Phe Leu Arg
                165                 170                 175 ggg aaa ctg aag ctg tac acg gga gag gtc tgc agg aga ggg gac agg     576
Gly Lys Leu Lys Leu Tyr Thr Gly Glu Val Cys Arg Arg Gly Asp Arg
            180                 185                 190 tga                                                                  579
```

<210> SEQ ID NO 6
<211> LENGTH: 1488
<212> TYPE: DNA
<213> ORGANISM: Artificial
<220> FEATURE:
<223> OTHER INFORMATION: Descritotion of artificial sequence: fusion
     polynucleotide of NK and mG-CSF
<220> FEATURE:
<221> NAME/KEY: CDS
<222> LOCATION: (1)..(1488)
<223> OTHER INFORMATION:

<400> SEQUENCE: 6

```
tcc cgg gag atg gcg ttc agc aac atg tct gcg cag gct gcc gga aaa      48
Ser Arg Glu Met Ala Phe Ser Asn Met Ser Ala Gln Ala Ala Gly Lys
 1               5                  10                  15 agc agt aca gaa aag aaa tac att gtc gga ttt aag cag aca atg agt      96
Ser Ser Thr Glu Lys Lys Tyr Ile Val Gly Phe Lys Gln Thr Met Ser
            20                  25                  30 gcc atg agt tcc gcc aag aaa aag gat gtt att tct gaa aaa ggc gga     144
Ala Met Ser Ser Ala Lys Lys Lys Asp Val Ile Ser Glu Lys Gly Gly
        35                  40                  45 aag gtt caa aag caa ttt aag tat gtt aac gcg gcc gca aca ttg         192
Lys Val Gln Lys Gln Phe Lys Tyr Val Asn Ala Ala Ala Thr Leu
    50                  55                  60 gat gaa aaa gct gta aaa gaa ttg aaa aaa gat ccg agc gtt gca tat     240
Asp Glu Lys Ala Val Lys Glu Leu Lys Lys Asp Pro Ser Val Ala Tyr
 65                  70                  75                  80 gtg gaa gaa gat cat att gca cat gaa tat gcg caa tct gtt cct tat     288
Val Glu Glu Asp His Ile Ala His Glu Tyr Ala Gln Ser Val Pro Tyr
                 85                  90                  95 ggc att tct caa att aaa gcg ccg gct ctt cac tct caa ggc tac aca     336
Gly Ile Ser Gln Ile Lys Ala Pro Ala Leu His Ser Gln Gly Tyr Thr
            100                 105                 110 ggc tct aac gta aaa gta gct gtt atc gac agc gga att gac tct tct     384
Gly Ser Asn Val Lys Val Ala Val Ile Asp Ser Gly Ile Asp Ser Ser
        115                 120                 125 cat cct gac tta aac gtc aga ggc gga gca agc ttc gtt cct tct gaa     432
His Pro Asp Leu Asn Val Arg Gly Gly Ala Ser Phe Val Pro Ser Glu
    130                 135                 140 aca aac cca tac cag gac ggc agt tct cac ggt acg cat gtc gcc ggt     480
Thr Asn Pro Tyr Gln Asp Gly Ser Ser His Gly Thr His Val Ala Gly
145                 150                 155                 160 acg att gcc gct ctt aat aac tca atc ggt gtt ctg ggc gta gcg cca     528
Thr Ile Ala Ala Leu Asn Asn Ser Ile Gly Val Leu Gly Val Ala Pro
                165                 170                 175 agc gca tca tta tat gca gta aaa gtg ctt gat tca aca gga agc ggc     576
Ser Ala Ser Leu Tyr Ala Val Lys Val Leu Asp Ser Thr Gly Ser Gly
            180                 185                 190 caa tat agc tgg att att aac ggc att gag tgg gcc att tcc aac aat     624
Gln Tyr Ser Trp Ile Ile Asn Gly Ile Glu Trp Ala Ile Ser Asn Asn
        195                 200                 205 atg gat gtt atc aac atg agc ctt ggc gga cct act ggt tct aca gcg     672
Met Asp Val Ile Asn Met Ser Leu Gly Gly Pro Thr Gly Ser Thr Ala
    210                 215                 220 ctg aaa aca gta gtt gat aaa gcg gtt tcc agc ggt atc gtc gtt gct     720
Leu Lys Thr Val Val Asp Lys Ala Val Ser Ser Gly Ile Val Val Ala
225                 230                 235                 240 gcc gca gcc gga aac gaa ggt tca tcc gga agc aca agc aca gtc ggc     768
Ala Ala Ala Gly Asn Glu Gly Ser Ser Gly Ser Thr Ser Thr Val Gly
                245                 250                 255 tac cct gca aaa tat cct tct act att gca gta ggt gcg gta aac agc     816
Tyr Pro Ala Lys Tyr Pro Ser Thr Ile Ala Val Gly Ala Val Asn Ser
            260                 265                 270 agc aac caa aga gct tca ttc tcc agc gta ggt tct gag ctt gat gta     864
Ser Asn Gln Arg Ala Ser Phe Ser Ser Val Gly Ser Glu Leu Asp Val
        275                 280                 285 atg gct cct ggc gtg tcc atc caa agc aca ctt cct gga ggc act tac     912
Met Ala Pro Gly Val Ser Ile Gln Ser Thr Leu Pro Gly Gly Thr Tyr
    290                 295                 300 ggc gct tat aac gga acg gtg gat ccg aat tct gtt ccc ctg gtc act     960
Gly Ala Tyr Asn Gly Thr Val Asp Pro Asn Ser Val Pro Leu Val Thr
```

```
gtc agc gct ctg cca cca tcc ctg cct ctg ccc cga agc ttc ctg ctt   1008
Val Ser Ala Leu Pro Pro Ser Leu Pro Leu Pro Arg Ser Phe Leu Leu
                325                 330                 335 aag tcc ctg gag caa gtg agg aag atc cag gcc agc ggc tcg gtg ctg   1056
Lys Ser Leu Glu Gln Val Arg Lys Ile Gln Ala Ser Gly Ser Val Leu
        340                 345                 350 ctg gag cag ttg tgt gcc acc tac aag ctg tgt cac ccc gag gag ctg   1104
Leu Glu Gln Leu Cys Ala Thr Tyr Lys Leu Cys His Pro Glu Glu Leu
                355                 360                 365 gtg ttg ctg ggc cac tct ctg ggg atc ccg aag gct tcc ctg agt ggc   1152
Val Leu Leu Gly His Ser Leu Gly Ile Pro Lys Ala Ser Leu Ser Gly
    370                 375                 380 tgc tct agc cag gcc ctg cag cag aca cag tgc cta agc cag ctc cac   1200
Cys Ser Ser Gln Ala Leu Gln Gln Thr Gln Cys Leu Ser Gln Leu His
385                 390                 395                 400 agt ggg ctc tgc ctc tac caa ggt ctc ctg cag gct cta tcg ggt att   1248
Ser Gly Leu Cys Leu Tyr Gln Gly Leu Leu Gln Ala Leu Ser Gly Ile
                405                 410                 415 tcc cct gcc ctg gcc ccc acc ttg gac ttg ctt cag ctg gat gtt gcc   1296
Ser Pro Ala Leu Ala Pro Thr Leu Asp Leu Leu Gln Leu Asp Val Ala
        420                 425                 430 aac ttt gcc acc acc atc tgg cag cag atg gaa aac cta ggg gtg gcc   1344
Asn Phe Ala Thr Thr Ile Trp Gln Gln Met Glu Asn Leu Gly Val Ala
                435                 440                 445 cct act gtg cag ccc aca cag agc gcc atg cca gcc ttc act tct gcc   1392
Pro Thr Val Gln Pro Thr Gln Ser Ala Met Pro Ala Phe Thr Ser Ala
    450                 455                 460 ttc cag cgc cgg gca gga ggt gtc ctg gcc att tcg tac ctg cag ggc   1440
Phe Gln Arg Arg Ala Gly Gly Val Leu Ala Ile Ser Tyr Leu Gln Gly
465                 470                 475                 480 ttc ctg gag acg gct cgc ctt gct ctg cac cac ttg gcc cag atc tcg   1488
Phe Leu Glu Thr Ala Arg Leu Ala Leu His His Leu Ala Gln Ile Ser
                485                 490                 495

<210> SEQ ID NO 7
<211> LENGTH: 1194
<212> TYPE: DNA
<213> ORGANISM: Artificial
<220> FEATURE:
<223> OTHER INFORMATION: Descritotion of artificial sequence: fusion
      polynucleotide of NK and mInsulin2
<220> FEATURE:
<221> NAME/KEY: CDS
<222> LOCATION: (1)..(1194)
<223> OTHER INFORMATION:

<400> SEQUENCE: 7 ggg atc ccc atg gcg ttc agc aac atg tct gcg cag gct gcc gga aaa    48
Gly Ile Pro Met Ala Phe Ser Asn Met Ser Ala Gln Ala Ala Gly Lys
1               5                   10                  15 agc agt aca gaa aag aaa tac att gtc gga ttt aag cag aca atg agt    96
Ser Ser Thr Glu Lys Lys Tyr Ile Val Gly Phe Lys Gln Thr Met Ser
            20                  25                  30 gcc atg agt tcc gcc aag aaa aag gat gtt att tct gaa aaa ggc gga   144
Ala Met Ser Ser Ala Lys Lys Lys Asp Val Ile Ser Glu Lys Gly Gly
        35                  40                  45 aag gtt caa aag caa ttt aag tat gtt aac gcg gcc gca gca aca ttg   192
Lys Val Gln Lys Gln Phe Lys Tyr Val Asn Ala Ala Ala Ala Thr Leu
    50                  55                  60 gat gaa aaa gct gta aaa gaa ttg aaa aaa gat ccg agc gtt gca tat   240
Asp Glu Lys Ala Val Lys Glu Leu Lys Lys Asp Pro Ser Val Ala Tyr
65                  70                  75                  80
```

-continued

| | |
|---|---|
| gtg gaa gaa gat cat att gca cat gaa tat gcg caa tct gtt cct tat<br>Val Glu Glu Asp His Ile Ala His Glu Tyr Ala Gln Ser Val Pro Tyr<br>85 90 95 | 288 |
| ggc att tct caa att aaa gcg ccg gct ctt cac tct caa ggc tac aca<br>Gly Ile Ser Gln Ile Lys Ala Pro Ala Leu His Ser Gln Gly Tyr Thr<br>100 105 110 | 336 |
| ggc tct aac gta aaa gta gct gtt atc gac agc gga att gac tct tct<br>Gly Ser Asn Val Lys Val Ala Val Ile Asp Ser Gly Ile Asp Ser Ser<br>115 120 125 | 384 |
| cat cct gac tta aac gtc aga ggc gga gca agc ttc gtt cct tct gaa<br>His Pro Asp Leu Asn Val Arg Gly Gly Ala Ser Phe Val Pro Ser Glu<br>130 135 140 | 432 |
| aca aac cca tac cag gac ggc agt tct cac ggt acg cat gtc gcc ggt<br>Thr Asn Pro Tyr Gln Asp Gly Ser Ser His Gly Thr His Val Ala Gly<br>145 150 155 160 | 480 |
| acg att gcc gct ctt aat aac tca atc ggt gtt ctg ggc gta gcg cca<br>Thr Ile Ala Ala Leu Asn Asn Ser Ile Gly Val Leu Gly Val Ala Pro<br>165 170 175 | 528 |
| agc gca tca tta tat gca gta aaa gtg ctt gat tca aca gga agc ggc<br>Ser Ala Ser Leu Tyr Ala Val Lys Val Leu Asp Ser Thr Gly Ser Gly<br>180 185 190 | 576 |
| caa tat agc tgg att att aac ggc att gag tgg gcc att tcc aac aat<br>Gln Tyr Ser Trp Ile Ile Asn Gly Ile Glu Trp Ala Ile Ser Asn Asn<br>195 200 205 | 624 |
| atg gat gtt atc aac atg agc ctt ggc gga cct act ggt tct aca gcg<br>Met Asp Val Ile Asn Met Ser Leu Gly Gly Pro Thr Gly Ser Thr Ala<br>210 215 220 | 672 |
| ctg aaa aca gta gtt gat aaa gcg gtt tcc agc ggt atc gtc gtt gct<br>Leu Lys Thr Val Val Asp Lys Ala Val Ser Ser Gly Ile Val Val Ala<br>225 230 235 240 | 720 |
| gcc gca gcc gga aac gaa ggt tca tcc gga agc aca agc aca gtc ggc<br>Ala Ala Ala Gly Asn Glu Gly Ser Ser Gly Ser Thr Ser Thr Val Gly<br>245 250 255 | 768 |
| tac cct gca aaa tat cct tct act att gca gta ggt gcg gta aac agc<br>Tyr Pro Ala Lys Tyr Pro Ser Thr Ile Ala Val Gly Ala Val Asn Ser<br>260 265 270 | 816 |
| agc aac caa aga gct tca ttc tcc agc gta ggt tct gag ctt gat gta<br>Ser Asn Gln Arg Ala Ser Phe Ser Ser Val Gly Ser Glu Leu Asp Val<br>275 280 285 | 864 |
| atg gct cct ggc gtg tcc atc caa agc aca ctt cct gga ggc act tac<br>Met Ala Pro Gly Val Ser Ile Gln Ser Thr Leu Pro Gly Gly Thr Tyr<br>290 295 300 | 912 |
| ggc gct tat aac gga acg agg aat tcc cag cac ctt tgt ggt tcc cac<br>Gly Ala Tyr Asn Gly Thr Arg Asn Ser Gln His Leu Cys Gly Ser His<br>305 310 315 320 | 960 |
| ctg gtg gag gct ctc tac ctg gtg tgt ggg gag cgt ggc ttc ttc tac<br>Leu Val Glu Ala Leu Tyr Leu Val Cys Gly Glu Arg Gly Phe Phe Tyr<br>325 330 335 | 1008 |
| aca ccc atg tcc cgc cgt gaa gtg gag gac cca caa gtg gca caa ctg<br>Thr Pro Met Ser Arg Arg Glu Val Glu Asp Pro Gln Val Ala Gln Leu<br>340 345 350 | 1056 |
| gag ctg ggt gga ggc ccg gga gca ggt gac ctt cag acc ttg gca ctg<br>Glu Leu Gly Gly Gly Pro Gly Ala Gly Asp Leu Gln Thr Leu Ala Leu<br>355 360 365 | 1104 |
| gag gtg gcc cag cag aag cgt ggc att gta gat cag tgc tgc acc agc<br>Glu Val Ala Gln Gln Lys Arg Gly Ile Val Asp Gln Cys Cys Thr Ser<br>370 375 380 | 1152 |
| atc tgc tcc ctc tac cag ctg gag aac tac tgc tcc cgg gtc<br>Ile Cys Ser Leu Tyr Gln Leu Glu Asn Tyr Cys Ser Arg Val<br>385 390 395 | 1194 |

<210> SEQ ID NO 8
<211> LENGTH: 1194
<212> TYPE: DNA
<213> ORGANISM: Artificial
<220> FEATURE:
<223> OTHER INFORMATION: Descritotion of artificial sequence: fusion
      polynucleotide of NK and MInsulin2
<220> FEATURE:
<221> NAME/KEY: CDS
<222> LOCATION: (1)..(1194)
<223> OTHER INFORMATION:

<400> SEQUENCE: 8

```
tcc cgg gag atg gcg ttc agc aac atg tct gcg cag gct gcc gga aaa      48
Ser Arg Glu Met Ala Phe Ser Asn Met Ser Ala Gln Ala Ala Gly Lys
1               5                   10                  15 agc agt aca gaa aag aaa tac att gtc gga ttt aag cag aca atg agt      96
Ser Ser Thr Glu Lys Lys Tyr Ile Val Gly Phe Lys Gln Thr Met Ser
            20                  25                  30 gcc atg agt tcc gcc aag aaa aag gat gtt att tct gaa aaa ggc gga     144
Ala Met Ser Ser Ala Lys Lys Lys Asp Val Ile Ser Glu Lys Gly Gly
        35                  40                  45 aag gtt caa aag caa ttt aag tat gtt aac gcg gcc gca gca aca ttg     192
Lys Val Gln Lys Gln Phe Lys Tyr Val Asn Ala Ala Ala Ala Thr Leu
    50                  55                  60 gat gaa aaa gct gta aaa gaa ttg aaa aaa gat ccg agc gtt gca tat     240
Asp Glu Lys Ala Val Lys Glu Leu Lys Lys Asp Pro Ser Val Ala Tyr
65                  70                  75                  80 gtg gaa gaa gat cat att gca cat gaa tat gcg caa tct gtt cct tat     288
Val Glu Glu Asp His Ile Ala His Glu Tyr Ala Gln Ser Val Pro Tyr
                85                  90                  95 ggc att tct caa att aaa gcg ccg gct ctt cac tct caa ggc tac aca     336
Gly Ile Ser Gln Ile Lys Ala Pro Ala Leu His Ser Gln Gly Tyr Thr
            100                 105                 110 ggc tct aac gta aaa gta gct gtt atc gac agc gga att gac tct tct     384
Gly Ser Asn Val Lys Val Ala Val Ile Asp Ser Gly Ile Asp Ser Ser
        115                 120                 125 cat cct gac tta aac gtc aga ggc gga gca agc ttc gtt cct tct gaa     432
His Pro Asp Leu Asn Val Arg Gly Gly Ala Ser Phe Val Pro Ser Glu
    130                 135                 140 aca aac cca tac cag gac ggc agt tct cac ggt acg cat gtc gcc ggt     480
Thr Asn Pro Tyr Gln Asp Gly Ser Ser His Gly Thr His Val Ala Gly
145                 150                 155                 160 acg att gcc gct ctt aat aac tca atc ggt gtt ctg ggc gta gcg cca     528
Thr Ile Ala Ala Leu Asn Asn Ser Ile Gly Val Leu Gly Val Ala Pro
                165                 170                 175 agc gca tca tta tat gca gta aaa gtg ctt gat tca aca gga agc ggc     576
Ser Ala Ser Leu Tyr Ala Val Lys Val Leu Asp Ser Thr Gly Ser Gly
            180                 185                 190 caa tat agc tgg att att aac ggc att gag tgg gcc att tcc aac aat     624
Gln Tyr Ser Trp Ile Ile Asn Gly Ile Glu Trp Ala Ile Ser Asn Asn
        195                 200                 205 atg gat gtt atc aac atg agc ctt ggc gga cct act ggt tct aca gcg     672
Met Asp Val Ile Asn Met Ser Leu Gly Gly Pro Thr Gly Ser Thr Ala
    210                 215                 220 ctg aaa aca gta gtt gat aaa gcg gtt tcc agc ggt atc gtc gtt gct     720
Leu Lys Thr Val Val Asp Lys Ala Val Ser Ser Gly Ile Val Val Ala
225                 230                 235                 240 gcc gca gcc gga aac gaa ggt tca tcc gga agc aca agc aca gtc ggc     768
Ala Ala Ala Gly Asn Glu Gly Ser Ser Gly Ser Thr Ser Thr Val Gly
                245                 250                 255
```

```
tac cct gca aaa tat cct tct act att gca gta ggt gcg gta aac agc      816
Tyr Pro Ala Lys Tyr Pro Ser Thr Ile Ala Val Gly Ala Val Asn Ser
        260                 265                 270 agc aac caa aga gct tca ttc tcc agc gta ggt tct gag ctt gat gta      864
Ser Asn Gln Arg Ala Ser Phe Ser Ser Val Gly Ser Glu Leu Asp Val
        275                 280                 285 atg gct cct ggc gtg tcc atc caa agc aca ctt cct gga ggc act tac      912
Met Ala Pro Gly Val Ser Ile Gln Ser Thr Leu Pro Gly Gly Thr Tyr
        290                 295                 300 ggc gct tat aac gga acg gtg gat ccg cag cac ctt tgt ggt tcc cac      960
Gly Ala Tyr Asn Gly Thr Val Asp Pro Gln His Leu Cys Gly Ser His
305                 310                 315                 320 ctg gtg gag gct ctc tac ctg gtg tgt ggg gag cgt ggc ttc ttc tac     1008
Leu Val Glu Ala Leu Tyr Leu Val Cys Gly Glu Arg Gly Phe Phe Tyr
                325                 330                 335 aca ccc atg tcc cgc gtg aaa gtg gag gac cca caa gtg gca caa ctg     1056
Thr Pro Met Ser Arg Val Lys Val Glu Asp Pro Gln Val Ala Gln Leu
        340                 345                 350 gag ctg ggt gga ggc ccg gga gca ggt gac ctt cag acc ttg gca ctg     1104
Glu Leu Gly Gly Gly Pro Gly Ala Gly Asp Leu Gln Thr Leu Ala Leu
        355                 360                 365 gag gtg gcc cag cag aag cgt ggc att gta gat cag tgc tgc acc agc     1152
Glu Val Ala Gln Gln Lys Arg Gly Ile Val Asp Gln Cys Cys Thr Ser
        370                 375                 380 atc tgc tcc ctc tac cag ctg gag aac tac tgc ccg aat tct             1194
Ile Cys Ser Leu Tyr Gln Leu Glu Asn Tyr Cys Pro Asn Ser
385                 390                 395

<210> SEQ ID NO 9
<211> LENGTH: 1356
<212> TYPE: DNA
<213> ORGANISM: Artificial
<220> FEATURE:
<223> OTHER INFORMATION: Descritotion of artificial sequence: fusion
      polynucleotide NK and mAdiponectin
<220> FEATURE:
<221> NAME/KEY: CDS
<222> LOCATION: (1)..(1356)
<223> OTHER INFORMATION:

<400> SEQUENCE: 9 tcc cgg gag atg gcg ttc agc aac atg tct gcg cag gct gcc gga aaa       48
Ser Arg Glu Met Ala Phe Ser Asn Met Ser Ala Gln Ala Ala Gly Lys
1               5                   10                  15 agt agt aca gaa aag aaa tac att gtc gga ttt aag cag aca atg agt       96
Ser Ser Thr Glu Lys Lys Tyr Ile Val Gly Phe Lys Gln Thr Met Ser
            20                  25                  30 gcc atg agt tcc gcc aag aaa aag gat gtt att tct gaa aaa ggc gga      144
Ala Met Ser Ser Ala Lys Lys Lys Asp Val Ile Ser Glu Lys Gly Gly
        35                  40                  45 aag gtt caa aag caa ttt aag tat gtt aac gcg gcc gca aca ttg          192
Lys Val Gln Lys Gln Phe Lys Tyr Val Asn Ala Ala Ala Thr Leu
    50                  55                  60 gat gaa aaa gct gta aaa gaa ttg aaa aaa gat ccg agc gtt gca tat      240
Asp Glu Lys Ala Val Lys Glu Leu Lys Lys Asp Pro Ser Val Ala Tyr
65                  70                  75                  80 gtg gaa gaa gat cat att gca cat gaa tat gcg caa tct gtt cct tat      288
Val Glu Glu Asp His Ile Ala His Glu Tyr Ala Gln Ser Val Pro Tyr
                85                  90                  95 ggc att tct caa att aaa gcg ccg gct ctt cac tct caa ggc tac aca      336
Gly Ile Ser Gln Ile Lys Ala Pro Ala Leu His Ser Gln Gly Tyr Thr
            100                 105                 110 ggc tct aac gta aaa gta gct gtt atc gac agc gga att gac tct tct      384
Gly Ser Asn Val Lys Val Ala Val Ile Asp Ser Gly Ile Asp Ser Ser
```

```
               Gly Ser Asn Val Lys Val Ala Val Ile Asp Ser Gly Ile Asp Ser Ser
                           115                 120                 125 cat cct gac tta aac gtc aga ggc gga gca agc ttc gtt cct tct gaa         432
His Pro Asp Leu Asn Val Arg Gly Gly Ala Ser Phe Val Pro Ser Glu
    130                 135                 140 aca aac cca tac cag gac ggc agt tct cac ggt acg cat gtc gcc ggt         480
Thr Asn Pro Tyr Gln Asp Gly Ser Ser His Gly Thr His Val Ala Gly
145                 150                 155                 160 acg att gcc gct ctt aat aac tca atc ggt gtt ctg ggc gta gcg cca         528
Thr Ile Ala Ala Leu Asn Asn Ser Ile Gly Val Leu Gly Val Ala Pro
                165                 170                 175 agc gca tca tta tat gca gta aaa gtg ctt gat tca aca gga agc ggc         576
Ser Ala Ser Leu Tyr Ala Val Lys Val Leu Asp Ser Thr Gly Ser Gly
            180                 185                 190 caa tat agc tgg att att aac ggc att gag tgg gcc att tcc aac aat         624
Gln Tyr Ser Trp Ile Ile Asn Gly Ile Glu Trp Ala Ile Ser Asn Asn
        195                 200                 205 atg gat gtt atc aac atg agc ctt ggc gga cct act ggt tct aca gcg         672
Met Asp Val Ile Asn Met Ser Leu Gly Gly Pro Thr Gly Ser Thr Ala
210                 215                 220 ctg aaa aca gta gtt gat aaa gcg gtt tcc agc ggt atc gtc gtt gct         720
Leu Lys Thr Val Val Asp Lys Ala Val Ser Ser Gly Ile Val Val Ala
225                 230                 235                 240 gcc gca gcc gga aac gaa ggt tca tcc gga agc aca agc aca gtc ggc         768
Ala Ala Ala Gly Asn Glu Gly Ser Ser Gly Ser Thr Ser Thr Val Gly
                245                 250                 255 tac cct gca aaa tat cct tct act att gca gta ggt gcg gta aac agc         816
Tyr Pro Ala Lys Tyr Pro Ser Thr Ile Ala Val Gly Ala Val Asn Ser
            260                 265                 270 agc aac caa aga gct tca ttc tcc agc gta ggt tct gag ctt gat gta         864
Ser Asn Gln Arg Ala Ser Phe Ser Ser Val Gly Ser Glu Leu Asp Val
        275                 280                 285 atg gct cct ggc gtg tcc atc caa agc aca ctt cct gga ggc act tac         912
Met Ala Pro Gly Val Ser Ile Gln Ser Thr Leu Pro Gly Gly Thr Tyr
290                 295                 300 ggc gct tat aac gga acg gtg gat ccg gcc gct tat atg tat cgc tca         960
Gly Ala Tyr Asn Gly Thr Val Asp Pro Ala Ala Tyr Met Tyr Arg Ser
305                 310                 315                 320 gcg ttc agt gtg ggg ctg gag acc cgc gtc act gtt ccc aat gta ccc        1008
Ala Phe Ser Val Gly Leu Glu Thr Arg Val Thr Val Pro Asn Val Pro
                325                 330                 335 att cgc ttt act aag atc ttc tac aac caa cag aat cat tat gac ggc        1056
Ile Arg Phe Thr Lys Ile Phe Tyr Asn Gln Gln Asn His Tyr Asp Gly
            340                 345                 350 agc act ggc aag ttc tac tgc aac att ccg gga ctc tac tac ttc tct        1104
Ser Thr Gly Lys Phe Tyr Cys Asn Ile Pro Gly Leu Tyr Tyr Phe Ser
        355                 360                 365 tac cac atc acg gtg tac atg aaa gat gtg aag gtg agc ctc ttc aag        1152
Tyr His Ile Thr Val Tyr Met Lys Asp Val Lys Val Ser Leu Phe Lys
370                 375                 380 aag gac aag gcc gtt ctc ttc acc tac gac cag tat cag gaa aag aat        1200
Lys Asp Lys Ala Val Leu Phe Thr Tyr Asp Gln Tyr Gln Glu Lys Asn
385                 390                 395                 400 gtg gac cag gcc tct ggc tct gtg ctc ctc cat ctg gag gtg gga gac        1248
Val Asp Gln Ala Ser Gly Ser Val Leu Leu His Leu Glu Val Gly Asp
                405                 410                 415 caa gtc tgg ctc cag gtg tat ggg gat ggg gac cac aat gga ctc tat        1296
Gln Val Trp Leu Gln Val Tyr Gly Asp Gly Asp His Asn Gly Leu Tyr
            420                 425                 430 gca gat aac gtc aac gac tct aca ttt act ggc ttt ctt ctc tac cat        1344
```

```
Ala Asp Asn Val Asn Asp Ser Thr Phe Thr Gly Phe Leu Leu Tyr His
        435                 440                 445 gat ccg aat tct                                                          1356
Asp Pro Asn Ser
    450
```